(12) United States Patent
Li

(10) Patent No.: US 12,358,916 B2
(45) Date of Patent: Jul. 15, 2025

(54) SUBSTITUTED HETEROCYCLE FUSED GAMMA-CARBOLINES SYNTHESIS

(71) Applicant: INTRA-CELLULAR THERAPIES, INC., New York, NY (US)

(72) Inventor: Peng Li, New Milford, NJ (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 955 days.

(21) Appl. No.: 17/415,669

(22) PCT Filed: Dec. 17, 2019

(86) PCT No.: PCT/US2019/066889
§ 371 (c)(1),
(2) Date: Jun. 17, 2021

(87) PCT Pub. No.: WO2020/131895
PCT Pub. Date: Jun. 25, 2020

(65) Prior Publication Data
US 2022/0041600 A1    Feb. 10, 2022

Related U.S. Application Data

(60) Provisional application No. 62/780,688, filed on Dec. 17, 2018.

(51) Int. Cl.
C07D 471/16 (2006.01)

(52) U.S. Cl.
CPC .................. *C07D 471/16* (2013.01)

(58) Field of Classification Search
CPC .................................... C07D 471/16
See application file for complete search history.

(56) References Cited

U.S. PATENT DOCUMENTS

| | | | |
|---|---|---|---|
| 2,490,813 | A | 12/1949 | Hughes et al. |
| 3,299,078 | A | 1/1967 | Pachter |
| 3,813,392 | A | 5/1974 | Sellstedt et al. |
| 4,001,263 | A | 1/1977 | Plattner et al. |
| 4,183,936 | A | 1/1980 | Rajagopalan |
| 4,219,550 | A | 8/1980 | Rajagopalan |
| 4,238,607 | A | 12/1980 | Rajagopalan |
| 5,576,460 | A | 11/1996 | Buchwald et al. |
| 5,648,539 | A | 7/1997 | Goodbrand |
| 5,648,542 | A | 7/1997 | Goodbrand et al. |
| 5,654,482 | A | 8/1997 | Goodbrand |
| 5,705,697 | A | 1/1998 | Goodbrand et al. |
| 5,723,669 | A | 3/1998 | Goodbrand et al. |
| 5,723,671 | A | 3/1998 | Goodbrand et al. |
| 5,847,166 | A | 12/1998 | Buchwald et al. |
| 5,902,901 | A | 5/1999 | Goodbrand et al. |
| 6,043,370 | A | 3/2000 | Kubo et al. |
| 6,166,226 | A | 12/2000 | Buchwald et al. |
| 6,235,936 | B1 | 5/2001 | Buchwald et al. |
| 6,323,366 | B1 | 11/2001 | Wolfe et al. |
| 6,395,916 | B1 | 5/2002 | Buchwald et al. |
| 6,407,092 | B1 | 6/2002 | Hester et al. |
| 6,465,693 | B2 | 10/2002 | Buchwald et al. |
| 6,541,639 | B2 | 4/2003 | Zhou et al. |
| 6,548,493 | B1 | 4/2003 | Robichaud et al. |
| 6,552,017 | B1 | 4/2003 | Robichaud et al. |
| 6,699,852 | B2 | 3/2004 | Robichaud et al. |
| 6,713,471 | B1 | 3/2004 | Robichaud et al. |
| 6,759,554 | B2 | 7/2004 | Buchwald et al. |
| 6,762,329 | B2 | 7/2004 | Marcoux et al. |
| 6,849,619 | B2 | 2/2005 | Robichaud et al. |
| 6,867,298 | B2 | 3/2005 | Buchwald et al. |
| 6,888,032 | B2 | 5/2005 | Buchwald et al. |
| 6,946,560 | B2 | 9/2005 | Buchwald et al. |
| 7,071,186 | B2 | 7/2006 | Robichaud et al. |
| 7,081,455 | B2 | 7/2006 | Robichaud et al. |
| 7,115,784 | B2 | 10/2006 | Buchwald et al. |
| 7,183,282 | B2 | 2/2007 | Robichaud et al. |
| 7,223,870 | B2 | 5/2007 | Ghosh et al. |
| 7,223,879 | B2 | 5/2007 | Buchwald et al. |
| RE39,679 | E | 6/2007 | Robichaud et al. |
| RE39,680 | E | 6/2007 | Robichaud et al. |
| 7,238,690 | B2 | 7/2007 | Robichaud et al. |
| 7,247,731 | B2 | 7/2007 | Buchwald et al. |
| 7,323,608 | B2 | 1/2008 | Buchwald et al. |
| 7,375,226 | B2 | 5/2008 | Jolidon et al. |
| 7,592,454 | B2 | 9/2009 | Lee et al. |
| 8,309,722 | B2 | 11/2012 | Tomesch et al. |
| 8,648,077 | B2 | 2/2014 | Tomesch et al. |

(Continued)

FOREIGN PATENT DOCUMENTS

| GB | 1476087 | 6/1977 |
|---|---|---|
| WO | WO 2000/064899 | 11/2000 |

(Continued)

OTHER PUBLICATIONS

Rodriguez-Spong et al., "General principles of pharmaceutical solid polymorphism: a supramolecular perspective", *Advanced Drug Delivery Reviews*, 56(3), pp. 241-274, (2004).

Alastair J. Florence, "Polymorph screening in pharmaceutical development" European Pharmaceutical Review, Aug. 19, 2010, https://www.europeanpharmaceuticalreview.com/article/3659/polymorph-screening-in-pharmaceutical-development/ (retrieved on Mar. 7, 2018).

Avendano, C., et al., "The problem of the existence of C(Ar)-H . . . N Intramolecular Hydrogen Bonds in a Family of 9-Azaphenyl-9H-carbazoles," *J. Chem. Soc. Perkin Trans.*, vol. 2, pp. 1547-1555, (1993).

(Continued)

*Primary Examiner* — John S Kenyon

(74) *Attorney, Agent, or Firm* — Hoxie & Associates LLC

(57) ABSTRACT

The present invention provides improved methods for the preparation of substituted heterocycle fused gamma-carbolines, intermediates useful in producing them and methods for producing such intermediates and such heterocycle fused gamma-carbolines.

41 Claims, No Drawings

(56) References Cited

U.S. PATENT DOCUMENTS

| | | | |
|---|---|---|---|
| 8,779,139 | B2 | 7/2014 | Tomesch et al. |
| 8,993,572 | B2 | 3/2015 | Mates et al. |
| 9,199,995 | B2 | 12/2015 | Tomesch et al. |
| 9,315,504 | B2 | 4/2016 | Tomesch et al. |
| 9,428,506 | B2 | 8/2016 | Mates et al. |
| 9,586,960 | B2 | 3/2017 | Tomesch et al. |
| 9,708,322 | B2 | 7/2017 | Li et al. |
| 9,751,883 | B2 | 9/2017 | Tomesch et al. |
| 10,077,267 | B2 | 9/2018 | Mates et al. |
| 10,221,176 | B2 | 3/2019 | Tomesch et al. |
| 10,245,260 | B2 | 4/2019 | Yao et al. |
| 10,464,938 | B2 | 11/2019 | Tomesch et al. |
| 10,597,395 | B2 | 3/2020 | Tomesch et al. |
| 10,799,500 | B2 | 10/2020 | Yao et al. |
| 10,906,906 | B2 | 2/2021 | Li et al. |
| 10,961,245 | B2 | 3/2021 | Li et al. |
| 11,066,407 | B2 | 7/2021 | Tomesch et al. |
| 11,376,249 | B2 | 7/2022 | Li et al. |
| 11,407,751 | B2 | 8/2022 | Tomesch et al. |
| 11,427,587 | B2 | 8/2022 | Li et al. |
| 11,453,670 | B2 | 9/2022 | Li et al. |
| 11,773,095 | B2 | 10/2023 | Li et al. |
| 11,844,757 | B2 | 12/2023 | Yao et al. |
| 2019/0112309 | A1 | 4/2019 | Peng et al. |
| 2019/0231780 | A1 | 8/2019 | Yao et al. |
| 2020/0102309 | A1 | 4/2020 | Li et al. |
| 2021/0009592 | A1 | 1/2021 | Li et al. |
| 2021/0070755 | A1 | 3/2021 | Berecz et al. |
| 2021/0093634 | A1 | 4/2021 | Snyder et al. |
| 2022/0048910 | A1 | 2/2022 | Li et al. |
| 2022/0056031 | A1 | 2/2022 | Li et al. |
| 2022/0064166 | A1 | 3/2022 | Li |
| 2022/0088014 | A1 | 3/2022 | Li et al. |
| 2022/0160704 | A2 | 5/2022 | Torralva |
| 2022/0184072 | A1 | 6/2022 | Davis et al. |

FOREIGN PATENT DOCUMENTS

| | | | | |
|---|---|---|---|---|
| WO | WO-2017132408 | A1 * | 8/2017 | ........... A61K 31/445 |
| WO | WO-2019183341 | A1 * | 9/2019 | ......... A61K 31/4985 |
| WO | WO 2020/131895 | | 6/2020 | |
| WO | WO 2022/261633 | | 12/2022 | |
| WO | WO 2023/069880 | | 4/2023 | |
| WO | WO 2023/178111 | | 9/2023 | |
| WO | WO 2023/178113 | | 9/2023 | |

OTHER PUBLICATIONS

Bastin, R., et al.,"Salt Selection and Optimisation Procedures for Pharmaceutical New Chemical Entities", Organic Process and Research Development, vol. 4, No. 5, pp. 427-435 (2000).
Beletskaya, I.P., et al., "Pd- and Cu-catalyzed selective arylation of benzotriazole," Tetrahedron Letters, vol. 39, pp. 5617-5620, (1998).
Berger et al. "Synthesis of some conformationally restricted analogs of fentanyl." Journal of Medicinal Chemistry, vol. 20, No. 4, p. 600-602. 1977.
Boger, D., et al., J. Org. Chem., vol. 50, pp. 5782-5789, (1985).
Bowman, W.R., et al., "Copper (1) Catalysed Aromatic Nucleophilic Substitution: A Mechanistic and Synthetic Comparison with the $S_{RN}1$ Reaction", Tetrahedron Letters, vol. 25(50) p. 5821-5824, (1984).
Bowman, W.R., et al., "Intramolecular Aromatic Substitution ($S_{RN}1$) Reactions—Use of Entrainment for the Preparation of Benzothiazoles," Tetrahedron Letters, vol. 23, pp. 5093-5096, (1982).
Bowman, W.R., et al.,"Synthesis of 1H-quinazoline-4-ones using intramolecular aromatic nucelophilic substitution," ARKIVOC, vol. x, pp. 434-442 (2003).
Crawford, K., et al., "Copper-Catalyzed amidations of bromo substituted furans and thiophenes", Tetrahedron Letters, vol. 43, p. 7365-7368, (2002).
Evindar, G., et al., "Copper- and Palladium-Catalyzed Intramolecular Aryl Guanidinylation: An Efficient Method for the Synthesis of 2-Aminobenzimidazoles", Organic Letters, vol. 5, No. 2, p. 133-136, (2003).

Ezquerra, J., et al., "Efficient Reagents for the Synthesis of 5-, 7-, and 5, 7-Substitued Indoles Starting from Aromatic Amines: Scope and Limitations", J. Org. Chem., vol. 61, p. 5804-5812, (1996).
Fee, W.W., et al., "Copper(II)-promoted solvolyses of nickel(II) complexes III. Tetradentate Schiff base ligands containing various diamine segments," Aust. J. Chem., vol. 26, pp. 1475-1485, (1973).
Ferreira, I., et al., "Novel synthetic routes to thienocarbazoles via palladium or copper catalyzed amination or amidation of arylhalides and intramolecular cyclization", Tetrahedron, vol. 58, p. 7943-7949, (2002).
Finet, J-P., et al., "Recent advances in ullmann reaction: copper(II) diacetate catalysed N-, )- and S-arylation involving polycoordinate heteroatomic derivatives," Current Organic Chemistry, vol. 6, pp. 597-626, (2002).
Goodbrand, H.B., et al., "Ligand-Accelerated catalysis of the Ullmann condensation: Application to hole conducting triarylamines," J. Org. Chem., vol. 64, pp. 670-674, (1999).
Hamann, B.C., et al., J. Am. Chem. Soc. vol. 120, pp. 2694-2703, (1998).
Hartwig, J., "Palladium-catalyzed amination of aryl halides: Mechanism and rational catalyst design," Synlett, pp. 329-340, (1996).
Hassan, J., et al., "Aryl-aryl bond formation one century after the discovery of the ullmann reaction," Chem. Rev., vol. 102, pp. 1359-1469, (2002).
Haynes, et al., "Occurrence of Pharmaceutically Acceptable Anions and Cations in the Cambridge Structural Database", Journal of Pharmaceutical Sciences, vol. 94, No. 10, p. 2111-2120 (2005).
Ito, T., et al., "Studies of organic catalytic reactions. VI. The function of pyridine and copper in the Rosenmund-von Braun reaction," Bulletin of the Chemical Society of Japan vol. 41, pp. 419-423, (1968).
Ji, J., et al., "Selective amination of polyhalopyridines catalyzed by a palladium-xantphos complex," Organic Letters, vol. 5, No. 24, pp. 4611-4614, (2003).
Kametani, T., et al., Heterocycles, vol. 14 (3), pp. 277-280, (1980).
Kang, S-K., et al., "Copper-catalyzed N-arylation of aryl iodides with benzamides or nitrogen heterocycles in the presence of ethylendiamine," Synlett, No. 3, pp. 427-430, (2002).
Kiyomori, A., et al., "An efficient copper-catalyzed coupling of aryl halides with imidazoles," Tetrahedron Letters, vol. 40, pp. 2657-2660, (1999).
Klapars, A., et al., "A general and efficient copper catalyst for the amidation of aryl halides and the N-arylation of nitrogen heterocycles," J. Am. Chem. Soc., vol. 123, pp. 7727-7729, (2001).
Klapars, A., et al., "A general and efficient copper catalyst for the amidation of aryl halides," J. Am. Chem. Soc., vol. 124, pp. 7421-7428, (2002).
Kondratov, S.A., et al., "Nucleophilic substitution in the aromatic series. Lv. Reaction of o-nitrochlorobenzene with ammonia in the presence of copper compounds," Zhurnal Organidreskoi Khimii, vol. 51(11), pp. 2387-2390, (1979).
Kwong, F.Y., et al., "Mild and efficient copper-catalyzed amination of aryl bromides with primary alkylamines," Organic Letters, vol. 5, No. 6, pp. 793-796, (2003).
Lee, T., et al. "Novel, Highly Potent, Selective 5-$HT_{2A}$/$D_2$ Receptor Antagonists as Potential Atypical Antipsychotics," Bioorg. Med. Chem. Lett. vol. 13, pp. 767-770, (2003).
Li et al., "Discovery of a Tetracyclic Quinoxaline Derivative as a Potent and Orally Active Multifunctional Drug Candidate for the Treatment of Neuropsychiatric and Neurological Disorders", Journal of Medicinal Chemistry, vol. 57, p. 2670-2682 (2014).
Louie, J., et al., Tetrahedron Letters, vol. 36, No. 21, pp. 3609-3612, (1995).
Marcoux, J-F., et al., "A general copper-catalyzed synthesis of diaryl ethers," J. Am. Chem. Soc., vol. 119, pp. 10539-10540, (1997).
Mulrooney, C.A., "Recent developments in copper-catalyzed n-arylation with aryl halides," Essay—University of Pennsylvania.
Murakami, Y., et al., Chem. Pharm. Bull, vol. 43(8), pp. 1281-1286, (1995).
Sadighi, J.P., et al., "A highly active palladium catalyst system for the arylation of anilines," Tetrahedron Letters, vol. 39, pp. 5327-5330, (1998).

(56) References Cited

OTHER PUBLICATIONS

Sigel. H., et al., *Inorganic Chemistry*, vol. 13, No. 2, pp. 462-465 (1974).

Sugahara, M., et al., *Chem. Pharm. Bull.*, 45(4), pp. 719-721, (1997).

Wagaw, S., et al., "A palladium-catalyzed method for the preparation of indoles via the Fischer indole synthesis," *Journal of the American Chemical Society*, vol. 121, No. 44, pp. 10251-10263, (1999).

Wolfe, J.P., et al., "Intramolecular palladium-catalyzed aryl amination and aryl amidation," *Tetrahedron*, vol. 52, No. 21, pp. 7525-7546, (1996).

Wolfe, J.P., "An improved catalyst system for aromatic carbon-nitrogen bond formation: The possible involvement of bis(phosphine) palladium complexes as key intermediates," *JACS*, vol. 118, pp. 7215-7216, (1996).

Wolter, M., et al., "Synthesis of N-aryl hydrazides by copper-catalyzed coupling of hydrazides with aryl iodides," *Organic Letters*, vol. 3, No. 23, pp. 3803-3805, (2001).

Yamada, K., et al., "A mild copper-mediated intramolecular amination of aryl halides," *Synlett*, No. 2, pp. 231-234, (2002).

Yang, B.H., "The development of efficient protocols for the palladium-catalyzed cyclization reactions of secondary amides and carbamates," *Organic Letters*, vol. 1, No. 1, pp. 35-37, (1999).

Zhang, Z., et al., *Catalysis Communications*, vol. 6, pp. 784-787, (2005).

Khorana, et al., "Gamma-Carbolines: Binding at 5-HT5A Serotonin Receptors," *Bioorganic & Medicinal Chemistry*, vol. 11, pp. 717-722, p. 718 Table 1, (2003).

Mulrooney, C.A., "Recent developments in copper-catalyzed n-arylation with aryl halides," Essay—University of Pennsylvania, 4 pages, (2004).

Nagai et al. "Synthesis of 2,3,4,4a,5,9b-hexahydro-1H-pyrido[4,3-b] indole derivatives and their central nervous system activities." *Journal of Medicinal Chemistry*, vol. 22, No. 6, p. 677-683, (1979).

Pubchem, OPEN Chemistry Database, Compound Summary for CID-9953107, p. 3, pp. 1-9 (2006).

Pubchem, OPEN Chemistry Database, Compound Summary for CID-22036753, p. 4, (2007), 12 pages.

Pubchem, OPEN Chemistry Database, Compound Summary for SID 103920954 (2011) 6 pages.

Zaragoza Dörwald, F., "Side Reactions in Organic Synthesis: A Guide to Successful Synthesis Design," Wiley-VCH, 6 pages, (2005).

\* cited by examiner

SUBSTITUTED HETEROCYCLE FUSED GAMMA-CARBOLINES SYNTHESIS

CROSS-REFERENCE TO RELATED APPLICATIONS

This application is a U.S. National Stage application under 35 U.S.C. § 371 of International Application No. PCT/US2019/066889, filed on Dec. 17, 2019, which claims priority to and the benefit of U.S. Provisional Application No. 62/780,688, filed on Dec. 17, 2018, the contents of each of which are incorporated by reference in their entireties.

FIELD OF THE INVENTION

The present invention relates to a method for the preparation of particular substituted heterocycle fused gamma-carbolines, as described herein, which are useful in the treatment of diseases involving the 5-HT$_{2A}$ receptor, the serotonin transporter (SERT), pathways involving dopamine D$_1$ and/or D$_2$ receptor signaling systems, and/or the μ-opioid receptor.

BACKGROUND OF THE INVENTION

Substituted heterocycle fused gamma-carbolines are known to be agonists or antagonists of 5-HT$_2$ receptors, particularly 5-HT$_{2A}$ receptors, in treating central nervous system disorders. These compounds have been disclosed in U.S. Pat. Nos. 6,548,493; 7,238,690; 6,552,017; 6,713,471; 7,183,282; U.S. RE39680, and U.S. RE39679, as novel compounds useful for the treatment of disorders associated with 5-HT$_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity. U.S. Pat. Nos. 8,309,722, and 7,081,455, also disclose methods of making substituted heterocycle fused gamma-carbolines and uses of these gamma-carbolines as serotonin agonists and antagonists useful for the control and prevention of central nervous system disorders such as addictive behavior and sleep disorders.

In addition, U.S. Pat. No. 8,598,119 discloses use of particular substituted heterocycle fused gamma-carbolines for the treatment of a combination of psychosis and depressive disorders as well as sleep, depressive and/or mood disorders in patients with psychosis or Parkinson's disease. In addition to disorders associated with psychosis and/or depression, this patent application discloses and claims use of these compounds at a low dose to selectively antagonize 5-HT$_{2A}$ receptors without affecting or minimally affecting dopamine D$_2$ receptors, thereby useful for the treatment of sleep disorders without the side effects associated with high occupancy of the dopamine D$_2$ pathways or side effects of other pathways (e.g., GABAA receptors) associated with conventional sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pain, and chest pain. U.S. Pat. No. 8,648,077 also discloses methods of preparing toluenesulfonic acid addition salt crystals of these substituted heterocycle fused gamma-carbolines.

In addition, recent evidence shows that the aforementioned substituted fused heterocycle gamma carbolines may operate, in part, through NMDA receptor antagonism via mTOR1 signaling, in a manner similar to that of ketamine. Ketamine is a selective NMDA receptor antagonist. Ketamine acts through a system that is unrelated to the common psychogenic monoamines (serotonin, norepinephrine and dopamine), and this is a major reason for its much more rapid effects. Ketamine directly antagonizes extrasynaptic glutamatergic NMDA receptors, which also indirectly results in activation of AMPA-type glutamate receptors. The downstream effects involve the brain-derived neurotrophic factor (BDNF) and mTORC1 kinase pathways. Similar to ketamine, recent evidence suggests that compounds related to those of the present disclosure enhance both NMDA and AMPA-induced currents in rat medial prefrontal cortex pyramidal neurons via activation of D1 receptors, and that this is associated with increased mTORC1 signaling. International application PCT/US2018/043100 discloses such effects for certain substituted fused heterocycle gamma-carbolines, and useful therapeutic indications related thereto.

The publication US 2017/319580 discloses additional substituted fused gamma carbolines. These newer compounds retain much of the unique pharmacologic activity of the previously disclosed compounds, including serotonin receptor inhibition, SERT inhibition, and dopamine receptor modulation. However, these compounds were found to unexpectedly also show significant activity at mu-opiate receptors. Analogs of these novel compounds have also been disclosed, for example, in publications WO 2018/126140 and WO 2018/126143.

For example, the Compound of Formula A, shown below, is a potent serotonin 5-HT$_{2A}$ receptor antagonist and mu-opiate receptor partial agonist or biased agonist. This compound also interacts with dopamine receptors, particular the dopamine D1 receptors.

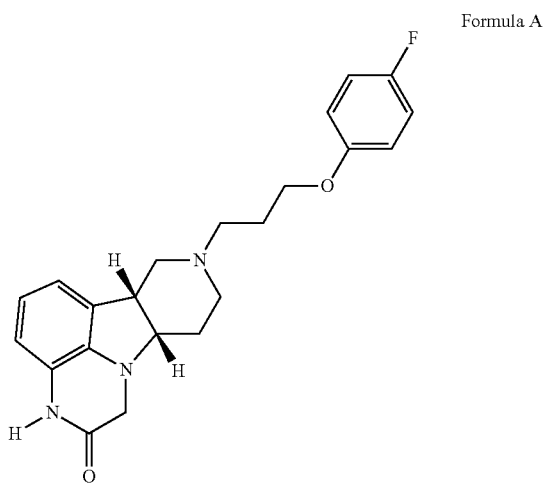 [SMILES: O=C1CN2c3c(cccc3[C@@H]3CN(CCCOc4ccc(F)cc4)CC[C@@H]32)N1]

Formula A

It is also believed that the Compound of Formula A, via its D$_1$ receptor activity, may also enhance NMDA and AMPA mediated signaling through the mTOR pathway. The Compound of Formula A is thus useful for the treatment or prophylaxis of central nervous system disorders, but there is a need in the art additional compounds having this unique biochemical and pharmacological profile, especially those which may have subtly altered pharmacologic or pharmacokinetic profiles compared to the Compound of Formula A.

The preparation of substituted heterocycle fused gamma-carbolines in free or pharmaceutically acceptable salt forms, intermediates used in their preparation, for example enantiomerically pure 2,3,4,4a,5,9b-hexahydro-1H-pyrido[4,3-b]indole type intermediates, and methods for producing said intermediates and said substituted heterocycle fused gamma-carbolines are disclosed in U.S. Pat. Nos. 7,183,282, 8,309,722, 8,779,139, 9,315,504, and 9,751,883, the entire contents of each of which are hereby incorporated by reference.

The present disclosure provides methods of preparing particular fused gamma-carbolines in high purity, yield and economic efficiency.

SUMMARY OF THE INVENTION

The present invention provides improved methods for the preparation of substituted heterocycle fused gamma-carbolines in free or pharmaceutically acceptable salt forms, intermediates used in their preparation, for example enantiomerically pure 2,3,4,4a,5,9b-hexahydro-1H-pyrido[4,3-b]indole type intermediates, and methods for producing said intermediates and said substituted heterocycle fused gamma-carbolines are disclosed in the present invention.

Substituted heterocycle fused gamma-carbolines and their pharmaceutically acceptable salts produced by the present invention are represented by the core structures shown in Formula 1J and 2J:

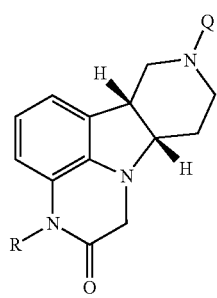

1J

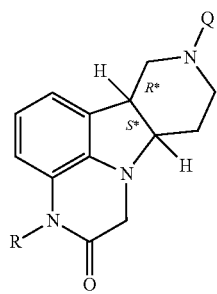

2J wherein R is selected from H and C$_{1-4}$alkyl, and Q is selected from 4-(4-fluorophenyl)-4-oxobutyl and 3-(4-fluorophenoxy)propyl. It is understood that in the compound of Formula 2J (and like Formula 2's herein throughout) the stereochemistry shown is absolute stereochemistry, which, for example, corresponds to the 4aS, 9bR configuration in the compound of Formula 2I, and the 6bR, 10aS configuration in the compound of Formula 2J. In contrast, it is understood that in the compound of Formula 1J (and like Formula 1's herein throughout) the stereochemistry shown is relative stereochemistry for the two adjacent stereocenters. Thus, for example, in the compound of Formula 1J shown above, the formula represents both compounds having the 6bR, 4aS configuration and compounds having the 6bS, 4aR configuration, or combinations thereof.

In some embodiments, the present invention pertains to compounds of Formula 1I, as shown below, in free or salt form, which are useful, e.g., as intermediates for the production of compounds of Formula 1J:

Compounds of Formula 1I:

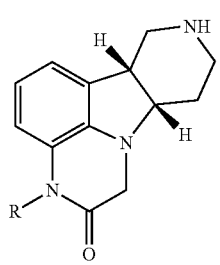

1I wherein:

R is H or C$_{1-4}$alkyl (e.g., methyl);

in free or salt form, e.g., in acid addition salt form, optionally in solid form.

In some embodiments, the invention further pertains to compounds of the following formulae:

1.1 Formula 1I, wherein R is C$_1$-C$_4$alkyl (e.g., methyl).

1.2 Formula 1I, wherein R is H.

1.3 Formula 1I, 1.1 or 1.2, wherein the compound is in free base form.

1.4 Formula 1I, 1.1 or 1.2, wherein the compound is in acid addition salt form.

1.5 Formula 1.4, wherein the acid addition salt form is a hydrohalide salt form (e.g., hydrochloride, hydrobromide, hydroiodide or hydrofluoride, e.g. in a base to acid molar ratio of 1:1 to 3:1).

1.6 Formula 1.5, wherein the acid addition salt form is a hydrochloride salt.

1.7 Any of the preceding formulae, wherein said compound is in solid form, e.g., solid amorphous form or solid crystalline form.

1.8 Any of the preceding formulae wherein said compounds are at least 70%, preferably at least 80%, more preferably at least 90%, most preferably greater than 95%, and up to 100%, cis stereoisomer relative to all other stereoisomers and/or wherein said compounds have an enantiomeric excess (e.e.) of at least 70%, preferably at least 80%, more preferably at least 90%, most preferably greater than 95% or greater than 97% or greater than 99%, or greater than 99.5%, or greater than 99.9%, and up to 100% (i.e., for the 4aS, 9bR enantiomer shown above).

In some embodiments, the present invention pertains to compounds of Formula 2I, as shown below, in free or salt form, which are useful, e.g., as intermediates for the production of compounds of Formula 2J:

Compounds of Formula 2I:

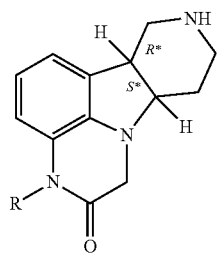

wherein:
R is H or $C_{1-4}$alkyl (e.g., methyl);
in free or salt form, e.g., in acid addition salt form, optionally in solid form.

The invention further pertains to compounds of the following formulae:

2.1 Formula 2I, wherein R is $C_1$-$C_4$alkyl (e.g., methyl).
2.2 Formula 2I, wherein R is H.
2.3 Formula 2I, 2.1 or 2.2, wherein the compound is in free base form.
2.4 Formula 2I, 2.1 or 2.2, wherein the compound is in acid addition salt form.
2.5 Formula 2.4, wherein the acid addition salt form is a hydrohalide salt form (e.g., hydrochloride, hydrobromide, hydroiodide or hydrofluoride, e.g. in a base to acid molar ratio of 1:1 to 3:1).
2.6 Formula 2.5, wherein the acid addition salt form is a hydrochloride salt.
2.7 Any of the preceding formulae, wherein said compound is in solid form, e.g., solid amorphous form or solid crystalline form.
2.8 Any of the preceding formulae wherein said compounds are at least 70%, preferably at least 80%, more preferably at least 90%, most preferably greater than 95%, and up to 100%, cis stereoisomer relative to all other stereoisomers.

The present invention further provides the following compounds, which may be formed as impurities in the processes for making the compounds of Formula 1J:

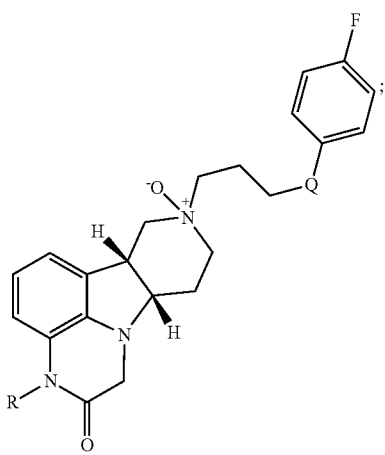

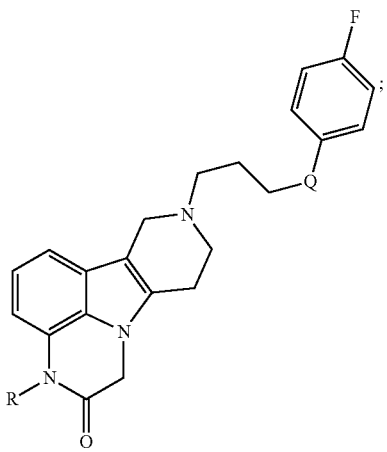

wherein, in each of said compounds 1K and 1L, the group R is selected from H and $C_{1-4}$ alkyl (e.g., methyl), and the group Q is selected from —O— and —(C=O)—.

The present invention further provides the following compounds, which may be formed as impurities in the processes for making the compounds of Formula 2J:

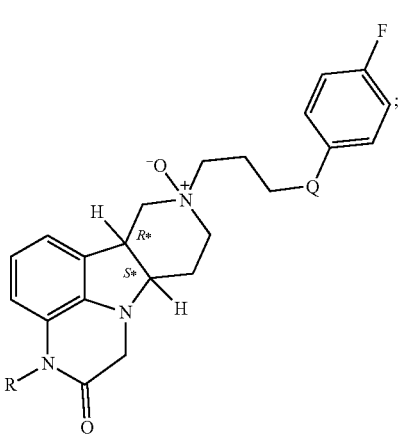

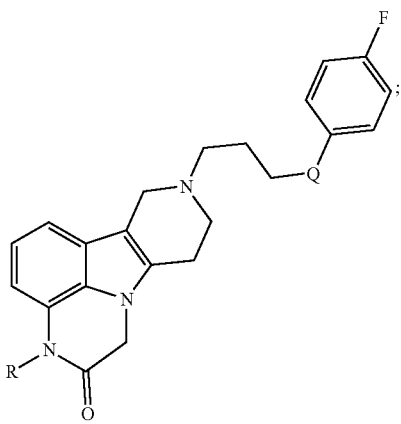

wherein, in each of said compounds 2K and 2L, the group R is selected from H and $C_{1-4}$ alkyl (e.g., methyl), and the group Q is selected from —O— and —(C=O)—.

In some embodiments, the present invention pertains to a method for preparing the compound of Formula 1J, as shown in the following scheme:

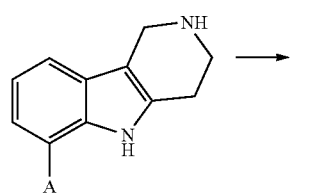

1A

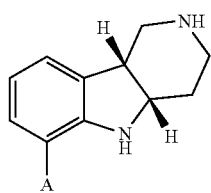

racemic cis
1B

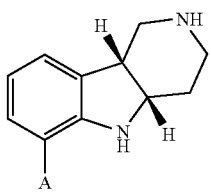

enantionmerically enriched
1C

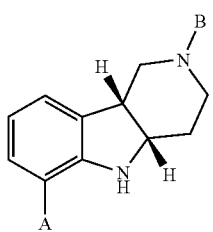

1D

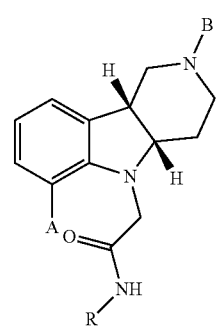

1E

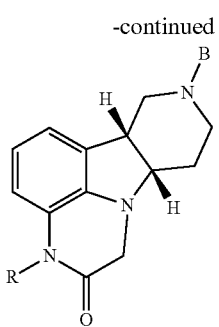

1F

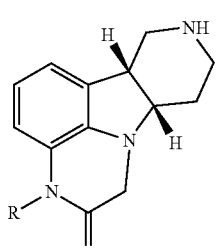

1I

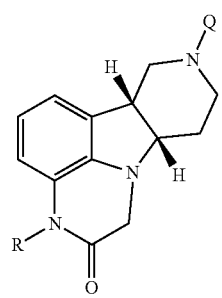

1J wherein for each of compounds 1A through 1J, independently:
(i) A is selected from Br, Cl and I;
(ii) R is selected from H and $C_{1-4}$alkyl (e.g. methyl);
(iii) B is a protecting group, as defined herein; and
(iv) Q is selected from 4-(4-fluorophenyl)-4-oxobutyl and 3-(4-fluorophenoxy)propyl;

wherein each of compounds 1A, 1B, 1C, 1D, 1E, 1F, 1I and 1J are independently in free base or salt form (e.g., acid addition salt form). It is understood that the compound 1B is substantially, essentially, or completely the racemic cis isomers, i.e., containing approximately equal amounts of the two cis enantiomers to the substantial or complete exclusion of any trans isomers. It is further understood that the compound 1C is substantially, essentially, or completely a single cis enantiomer, specifically the 4aS, 9bR enantiomer (as drawn above), to the substantial or complete exclusion of the opposite cis enantiomer or any trans stereoisomer.

In some embodiments, the present invention pertains to a method for preparing the compound of formula 2J, as shown in the following scheme:

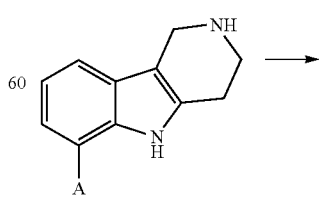

1A

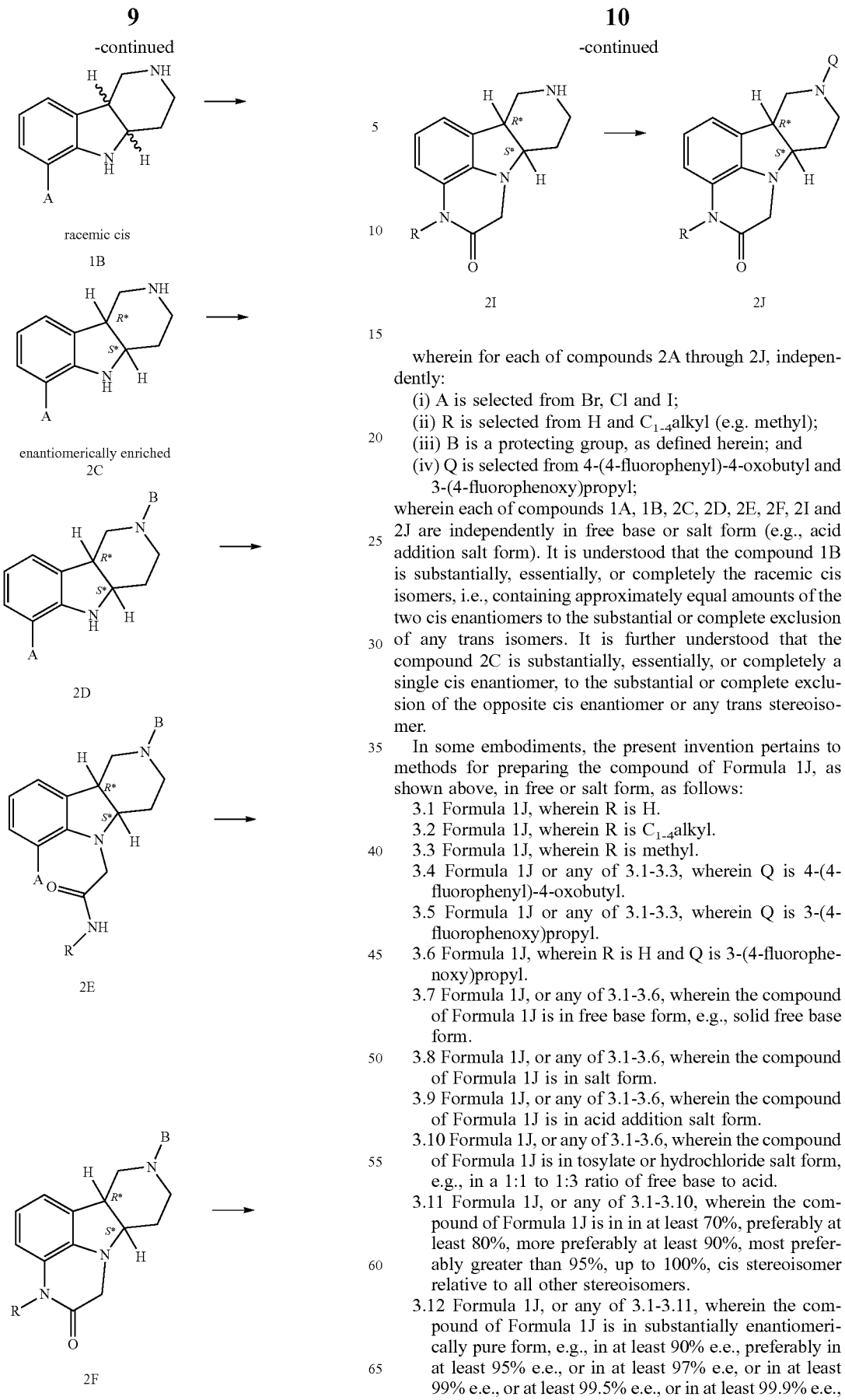

wherein for each of compounds 2A through 2J, independently:
(i) A is selected from Br, Cl and I;
(ii) R is selected from H and $C_{1-4}$alkyl (e.g. methyl);
(iii) B is a protecting group, as defined herein; and
(iv) Q is selected from 4-(4-fluorophenyl)-4-oxobutyl and 3-(4-fluorophenoxy)propyl;

wherein each of compounds 1A, 1B, 2C, 2D, 2E, 2F, 2I and 2J are independently in free base or salt form (e.g., acid addition salt form). It is understood that the compound 1B is substantially, essentially, or completely the racemic cis isomers, i.e., containing approximately equal amounts of the two cis enantiomers to the substantial or complete exclusion of any trans isomers. It is further understood that the compound 2C is substantially, essentially, or completely a single cis enantiomer, to the substantial or complete exclusion of the opposite cis enantiomer or any trans stereoisomer.

In some embodiments, the present invention pertains to methods for preparing the compound of Formula 1J, as shown above, in free or salt form, as follows:
3.1 Formula 1J, wherein R is H.
3.2 Formula 1J, wherein R is $C_{1-4}$alkyl.
3.3 Formula 1J, wherein R is methyl.
3.4 Formula 1J or any of 3.1-3.3, wherein Q is 4-(4-fluorophenyl)-4-oxobutyl.
3.5 Formula 1J or any of 3.1-3.3, wherein Q is 3-(4-fluorophenoxy)propyl.
3.6 Formula 1J, wherein R is H and Q is 3-(4-fluorophenoxy)propyl.
3.7 Formula 1J, or any of 3.1-3.6, wherein the compound of Formula 1J is in free base form, e.g., solid free base form.
3.8 Formula 1J, or any of 3.1-3.6, wherein the compound of Formula 1J is in salt form.
3.9 Formula 1J, or any of 3.1-3.6, wherein the compound of Formula 1J is in acid addition salt form.
3.10 Formula 1J, or any of 3.1-3.6, wherein the compound of Formula 1J is in tosylate or hydrochloride salt form, e.g., in a 1:1 to 1:3 ratio of free base to acid.
3.11 Formula 1J, or any of 3.1-3.10, wherein the compound of Formula 1J is in in at least 70%, preferably at least 80%, more preferably at least 90%, most preferably greater than 95%, up to 100%, cis stereoisomer relative to all other stereoisomers.
3.12 Formula 1J, or any of 3.1-3.11, wherein the compound of Formula 1J is in substantially enantiomerically pure form, e.g., in at least 90% e.e., preferably in at least 95% e.e., or in at least 97% e.e, or in at least 99% e.e., or at least 99.5% e.e., or in at least 99.9% e.e., up to 100% e.e.

In some embodiments, the present invention pertains to methods for preparing the compound of Formula 2J, as shown above, in free or salt form, as follows:

4.1 Formula 2J, wherein R is H.
4.2 Formula 2J, wherein R is $C_{1-4}$alkyl.
4.3 Formula 2J, wherein R is methyl.
4.4 Formula 2J or any of 4.1-4.3, wherein Q is 4-(4-fluorophenyl)-4-oxobutyl.
4.5 Formula 2J or any of 4.1-4.3, wherein Q is 3-(4-fluorophenoxy)propyl.
4.6 Formula 2J, wherein R is H and Q is 3-(4-fluorophenoxy)propyl.
4.7 Formula 2J, or any of 4.1-4.6, wherein the compound of Formula 2J is in free base form, e.g., solid free base form.
4.8 Formula 2J, or any of 4.1-4.6, wherein the compound of Formula 2J is in salt form.
4.9 Formula 2J, or any of 4.1-4.6, wherein the compound of Formula 2J is in acid addition salt form.
4.10 Formula 2J, or any of 4.1-4.6, wherein the compound of Formula 2J is in tosylate or hydrochloride salt form, e.g., in a 1:1 to 1:3 ratio of free base to acid.
4.11 Formula 2J, or any of 4.1-4.10, wherein the compound of Formula 2J is in in at least 70%, preferably at least 80%, more preferably at least 90%, most preferably greater than 95%, up to 100%, cis stereoisomer relative to all other stereoisomers.
4.12 Formula 2J, or any of 4.1-4.11, wherein the compound of Formula 2J is in substantially enantiomerically pure form, e.g., in at least 90% e.e., preferably in at least 95% e.e., or in at least 97% e.e, or in at least 99% e.e., or in at least 99.5%, or in at least 99.9% e.e., up to 100% e.e.

In a first aspect, the invention provides a method (Method 1J) for preparing a compound of Formula 1J, or any of 3.1-3.12, in free or salt form, comprising the steps of (a) reacting a compound of Formula 1E, in free or salt form, with (i) a transition metal catalyst selected from the group consisting of Groups 8-11 of the periodic table, (ii) optionally a base, (iii) optionally an alkali metal or ammonium iodide or bromide (e.g. potassium iodide or tetrabutylammonium bromide), and (iv) optionally a monodentate or bidentate ligand, to form an intermediate of Formula 1F, in free or salt form; (b) deprotecting the piperidine nitrogen of the compound of Formula 1F to yield the compound of Formula 1I (or any of 1.1-1.8), in free or salt form; and (c) alkylating the piperidine nitrogen of the compound of Formula 1I with a suitable alkylating agent to yield the compound of Formula 1J (or any of 3.1-3.12) in free or salt form; and optionally (d) converting the compound of Formula 1J in free form to a compound of Formula 1J (or any of 3.1-3.12) in salt form, e.g., acid addition salt form (e.g., tosylate salt form). In some embodiments, the method further comprises the step of alkylating a compound of Formula 1D to form the compound of Formula 1E.

In another embodiment of the first aspect, the invention provides a method (Method 2J) for preparing a compound of Formula 2J, or any of 4.1-4.12, in free or salt form, comprising the steps of (a) reacting a compound of Formula 2E, in free or salt form, with (i) a transition metal catalyst selected from the group consisting of Groups 8-11 of the periodic table, (ii) optionally a base, (iii) optionally an alkali metal or ammonium iodide or bromide (e.g. potassium iodide or tetrabutylammonium bromide), and (iv) optionally a monodentate or bidentate ligand, to form an intermediate of Formula 2F, in free or salt form; (b) deprotecting the piperidine nitrogen of the compound of Formula 2F to yield the compound of Formula 2I (or any of 2.1-2.8), in free or salt form; and (b) alkylating the piperidine nitrogen of the compound of Formula 1I with a suitable alkylating agent to yield the compound of Formula 2J (or any of 4.1-4.12) in free or salt form; and optionally (d) converting the compound of Formula 2J in free form to a compound of Formula 2J (or any of 4.1-4.12) in salt form, e.g., acid addition salt form (e.g., tosylate salt form). In some embodiments, the method further comprises the step of alkylating a compound of Formula 2D to form the compound of Formula 2E.

In a second aspect, the invention provides a method (Method 1I) for preparing a compound of Formula 1I, or any of 1.1-1.8, in free or salt form, comprising the steps of (a) reacting a compound of Formula 1E, in free or salt form, with (i) a transition metal catalyst selected from the group consisting of Groups 8-11 of the periodic table, (ii) optionally a base, (iii) optionally an alkali metal or ammonium iodide or bromide (e.g. potassium iodide or tetrabutylammonium bromide), and (iv) optionally a monodentate or bidentate ligand, to form an intermediate of Formula 1F, in free or salt form; and (b) deprotecting the piperidine nitrogen of the compound of Formula 1F to yield the compound of Formula 1I (or any of 1.1-1.8), in free or salt form. In some embodiments, the method further comprises the step of alkylating a compound of Formula 1D to form the compound of Formula 1E.

In another embodiment of the second aspect, the invention provides a method (Method 2I) for preparing a compound of Formula 2I, or any of 2.1-2.8, in free or salt form, comprising the steps of (a) reacting a compound of Formula 2E, in free or salt form, with (i) a transition metal catalyst selected from the group consisting of Groups 8-11 of the periodic table, (ii) optionally a base, (iii) optionally an alkali metal or ammonium iodide or bromide (e.g. potassium iodide or tetrabutylammonium bromide), and (iv) optionally a monodentate or bidentate ligand, to form an intermediate of Formula 2F, in free or salt form; and (b) deprotecting the piperidine nitrogen of the compound of Formula 2F to yield the compound of Formula 2I (or any of 2.1-2.8), in free or salt form. In some embodiments, the method further comprises the step of alkylating a compound of Formula 2D to form the compound of Formula 2E.

In a third aspect, the invention provides a method (Method 1F) for preparing a compound of Formula 1F, in free or salt form, comprising the steps of (a) reacting a compound of Formula 1E, in free or salt form, with (i) a transition metal catalyst selected from the group consisting of Groups 8-11 of the periodic table, (ii) optionally a base, (iii) optionally an alkali metal or ammonium iodide or bromide (e.g. potassium iodide or tetrabutylammonium bromide), and (iv) optionally a monodentate or bidentate ligand, to form an intermediate of Formula 1F, in free or salt form. In some embodiments, the method further comprises the step of alkylating a compound of Formula 1D to form the compound of Formula 1E.

In another embodiment of the third aspect, the invention provides a method (Method 2F) for preparing a compound of Formula 2F, in free or salt form, comprising the steps of (a) reacting a compound of Formula 2E, in free or salt form, with (i) a transition metal catalyst selected from the group consisting of Groups 8-11 of the periodic table, (ii) optionally a base, (iii) optionally an alkali metal or ammonium iodide or bromide (e.g. potassium iodide or tetrabutylammonium bromide), and (iv) optionally a monodentate or bidentate ligand, to form an intermediate of Formula 2F, in free or salt form. In some embodiments, the method further comprises the step of alkylating a compound of Formula 2D to form the compound of Formula 2E.

In another aspect, the present disclosure provides for the use of the Compound of Formula 1I, or any of 1.1 et seq., and/or the Compound of Formula 1F, in a process for the manufacture of a compound of Formula 1J, or any of 3.1-3.12.

In another aspect, the present disclosure provides for the use of the Compound of Formula 2I, or any of 2.1 et seq., and/or the Compound of Formula 1F, in a process for the manufacture of a compound of Formula 2J, or any of 4.1-4.12.

In another aspect, the present disclosure provides an active pharmaceutical composition comprising the compound of Formula 1J or 2J, in substantially pure form.

DETAILED DESCRIPTION OF THE INVENTION

In one aspect, the invention provides a method (Method 1I) for preparing a compound of Formula 1I, or any of 1.1-1.8, in free or salt form, comprising the steps of (a) reacting a compound of Formula 1E, in free or salt form, with (i) a transition metal catalyst selected from the group consisting of Groups 8-11 of the periodic table, (ii) optionally a base, (iii) optionally an alkali metal or ammonium iodide or bromide (e.g. potassium iodide or tetrabutylammonium bromide), and (iv) optionally a monodentate or bidentate ligand, to form an intermediate of Formula 1F, in free or salt form; and (b) deprotecting the piperidine nitrogen of the compound of Formula 1F to yield the compound of Formula 1I (or any of 1.1-1.8), in free or salt form. In some embodiments, the method further comprises the step of alkylating a compound of Formula 1D to form the compound of Formula 1E.

Preferably, steps (a) and (b) take place without isolation or without purification of the intermediate of the Formulas 1F. In some embodiments, the steps (a) and (b) take place sequentially in a single reaction vessel or a set of connected reaction vessels.

In another embodiment of this aspect, the invention provides a method (Method 2I) for preparing a compound of Formula 2I, or any of 2.1-2.8, in free or salt form, comprising the steps of (a) reacting a compound of Formula 2E, in free or salt form, with (i) a transition metal catalyst selected from the group consisting of Groups 8-11 of the periodic table, (ii) optionally a base, (iii) optionally an alkali metal or ammonium iodide or bromide (e.g. potassium iodide or tetrabutylammonium bromide), and (iv) optionally a monodentate or bidentate ligand, to form an intermediate of Formula 2F, in free or salt form; and (b) deprotecting the piperidine nitrogen of the compound of Formula 2F to yield the compound of Formula 2I (or any of 2.1-2.8), in free or salt form.

Preferably, steps (a) and (b) take place without isolation or without purification of the intermediate of the Formulas 2F. In some embodiments, the steps (a) and (b) take place sequentially in a single reaction vessel or a set of connected reaction vessels.

The transition metal catalyst of step (a) of Method 1I or 2I may be an atom, ion, salt or complex of transition metals selected from Groups 8-11 of the periodic table (e.g., palladium, copper, nickel, platinum, ruthenium, or rhodium). Examples of such transition metal catalyst include, but are not limited to copper catalysts such as CuI, CuCl, CuBr, CuBr$_2$, Cu(II) acetate, Cu$_2$Cl$_2$, Cu$_2$O, Cu, CuSO$_4$, Cu$_2$SO$_4$, or palladium or nickel catalysts such as Pd/C, PdCl$_2$, Pd(OAc)$_2$, (CH$_3$CN)$_2$PdCl$_2$, Pd[P(C$_6$H$_5$)$_3$]$_4$, bis(dibenzylideneacetone)palladium [Pd(dba)$_2$], tris(dibenzylideneacetone)dipalladium [Pd$_2$(dba)$_3$], Ni(acetylacetonate)$_2$, NiCl$_2$[P(C$_6$H$_5$)]$_2$ and Ni(1,5-cyclooctadiene)$_2$ as described in U.S. Pat. Nos. 6,759,554 B2, 6,395,916 B1, and 6,307,087 B1, each of which are herein incorporated by reference in their entirety. In a preferred embodiment, the transition metal catalyst is copper catalyst. In an especially preferred embodiment, said catalyst is CuI.

The base useful for step (a) of Method 1I or 2I may be a Bronsted base or a Lewis base, including by way of example only, amine bases (e.g. triethylamine, trimethylamine, N,N'-diisopropylethylamine, 1,8-diazabicyclo[5.4.0]undec-7-ene (DBU) or 1,4-diazabicyclo[2.2.2]octane (DABCO)), hydrides (e.g. sodium, lithium or potassium hydride), alkoxides (e.g. sodium or potassium tert-butoxide), carbonates (e.g. sodium carbonate or bicarbonate, potassium or cesium carbonate) or phosphates (e.g. potassium phosphate). In a preferred embodiment, the base is a carbonate of an alkali or alkali earth metal (e.g., sodium, potassium, cesium, barium, etc.). In an especially preferred embodiment, said base is potassium carbonate.

In some embodiments, the base for step (a) may be eliminated by using a ligand for step (a) which it itself basic, such as an amine ligand (e.g. DBU, DBN or a 1,2-diamine), as described below. In such embodiments, step (a) may comprise the ligand (iv) without a base (ii). In other embodiments, both a base (ii) and a basic ligand (iv) are used together, for example, an inorganic base (ii) (such as potassium carbonate or sodium carbonate) and a basic amine ligand (iv) (such as DBU, DBN or a 1,2-diamine).

The optional mono- or bi-dentate ligands useful in step (a) of Method 1I or 2I are those ligands known to ligate with transition metal catalysts. Examples of such ligands include, but are not limited to phenolic or amine ligands, such as optionally substituted aryl alcohol, 1,2-diamine, 1,2-aminoalcohol, 1,8-diazabicyclo[5.4.0]undec-7-ene (DBU), 1,5-diazabicyclo[4.3.0]non-5-ene (DBN), 1,4-diazabicyclo[2.2.2]octane (DABCO), imidazolium carbene, 4-(dimethylamino) pyridine, 2-(aminomethyl)pyridine, 4,7-diphenyl-1,10-phenanthroline, 4,7-dimethyl-1,10-phenanthroline, 5-methyl-1,10-phenanthroline, 5-chloro-1,10-phenanthroline, and 5-nitro-1,10-phenanthroline. For examples of phenolic or amine ligands include, but are not limited to, 2-phenylphenol, 2,6-dimethylphenol, 2-isopropylphenol, 1-naphthol, 8-hydroxyquinoline, 8-aminoquinoline, DBU, DBN, DABCO, 2-(dimethylamino)ethanol, N,N-diethyl salicylamide, 2-(dimethylamino)glycine, N,N,N',N'-tetramethyl-1,2-diaminoethane, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, (methylimino)diacetic acid, cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, N,N'-dimethyl-1,2-diaminoethane, N,N-dimethyl-2-hydroxybenzamide, N,N-diethyl-2-hydroxybenzamide, fluoro-N,N-diethyl-2-hydroxybenzamide, chloro-N,N'-diethyl-2-hydroxybenzamide, (2-hydroxyphenyl)(pyrrolidin-1-yl) methanone, biphenyl-2-ol, 2-pyridylphenol, 1,2-benezenediamine, ammonia, N,N-dimethylformamide, dimethylsulfoxide and 1-methyl-2-pyrrolidinone as described in U.S. Pat. Nos. 6,759,554B2; 6,395,916B1; 6,307,087B1, Klapars, A. et al., *J. Am. Chem. Soc.* (2002) 124, 7421-7428; Kang, S., et al., *Synlett*, 3, 427-430 (2002); Sugahara, *M. and Ukita, T., Chem. Pharm. Bull.* (1997) 45, 719-721, each of which is hereby incorporated by reference. In an especially preferred embodiment, said ligand is DBU, DBN, N,N'-dimethyl-1,2-diaminoethane, trans-N,N'-dimethyl-1,2-diaminocyclohexane, or N-butylethylenediamine. Without being bound to any theory, it is believed that the ligands facilitate the reaction by stabilizing and solubilizing the metal catalyst.

In some embodiment, the crude compound of Formula 1F or 2F is treated with a reagent to remove copper. For example, the crude compound may be suspended and/or dissolved in an organic solvent and washed with a basic aqueous solution (e.g., aqueous ammonia solution). Alternatively, the crude solid may be directly washed with a basic aqueous solution (e.g., aqueous ammonia solution).

The conditions for the deprotection step (b) of Method 1I or 2I necessarily varies with the choice of the protecting group B and may involve, for example, acid or base catalysis or catalytic hydrogenation. Thus, for example, wherein the protecting agent is an acyl group such as an alkanoyl or alkoxycarbonyl group (e.g., ethoxycarbonyl) or an aroyl group, deprotection may be accomplished, for example, by hydrolysis with a base such as an alkali metal hydroxide, for example lithium, potassium or sodium hydroxide. Alternatively, an acyl protecting agent such as a t-butoxycarbonyl group may be removed, for example, by treatment with a suitable acid, such as hydrochloric, sulfuric or phosphoric acid or trifluoroacetic acid. An arylmethoxycarbonyl protecting agent such as a benzyloxycarbonyl group may be removed, for example, by hydrogenation over a catalyst such as platinum or palladium-on-carbon, or by treatment with a Lewis acid such as boron tris(trifluoroacetate). For further examples of reagents useful for said deprotection step, see "Protective Groups in Organic Synthesis" by Theodora Green (publisher: John Wiley & Sons).

In a preferred embodiment, the protecting group B is a carbamate protecting group, for example, methoxycarbonyl, ethoxycarbonyl, propoxycarbonyl, isopropoxycarbonyl, or t-butoxycarbonyl. In said embodiment, step (b) of Method 1I or 2I may preferably be carried out using an acidic aqueous solution, such as aqueous hydrochloric acid or aqueous hydrobromic acid, or using a non-aqueous acidic medium, such as hydrogen chloride or hydrogen bromide in an organic solvent (e.g., methanol, THF, dioxane, diethyl ether, acetic acid, or a mixture thereof) or using a strong organic acid (e.g., neat trifluoroacetic acid (TFA), or TFA in a suitable organic solvent, e.g. dioxane). In a preferred embodiment, the non-aqueous acidic medium is hydrobromic acid dissolved in an organic solvent (e.g., in acetic acid).

In some embodiments, step (b) of Method 1I or 2I is carried out under acidic conditions and the compound of Formula 1I or 2I is obtained in the form of an acid addition salt. For example, the reaction can be carried out using hydrochloric acid or hydrobromic acid, resulting in the compound of Formula 1I or 2I as a hydrochloride or hydrobromide salt. In other embodiments, step (b) of Method 1I or 2I is carried out under acidic conditions and the reaction mixture is subjected to neutralization or basification with a suitable base in order to obtain the compound of Formula 1I or 2I in free base form. Suitable bases for carrying out said neutralization or basification include inorganic bases such as hydroxides, oxides, carbonates and bicarbonates (e.g., ammonium, alkali metal or alkaline earth metal bases, including NaOH, KOH, LiOH, NH$_4$OH, Ca(OH)$_2$, CaO, MgO, Na$_2$CO$_3$, K$_2$CO$_3$, Li$_2$CO$_3$, NaHCO$_3$, KHCO$_3$, LiHCO$_3$, CaCO$_3$, MgCO$_3$, (NH$_4$)$_2$CO$_3$, and the like), optionally in aqueous solution (such as aqueous sodium hydroxide, aqueous sodium carbonate, or aqueous ammonia).

In some embodiments, Method 1I or 2I provides the compounds of Formula 1I or 2I, respectively, as a crystalline free base or as a crystalline acid-addition salt, e.g., as a hydrochloride or hydrobromide salt. The inventors have unexpectedly found that use of the Method 1I or 2I, or one or more of Methods 5.1-5.52, results in the production of compounds of Formula 1I or 2I with much lower levels of contamination by transition metal impurities (e.g., copper) compared to prior art methods of making these compounds. For example, use of the present methods can result in the production of compounds of Formula 1I or 2I containing less than about 50 ppm of copper, or less than about 10 ppm of copper, or less than about 5 ppm of copper.

In specific embodiments of the first aspect, the present disclosure provides:

5.1 Method 1I or 2I, wherein the compound of Formula 1I or 2I is, respectively, a compound according to any of Formula 1.1-1.8 or 2.1-2.8.

5.2 Method 1I or 2I, wherein the substituent A of the compound of Formula 1E or 2E is selected from Br, Cl and I.

5.3 Method 5.2, wherein A is Br.

5.4 Method 1I or 2I, or any of 5.1 et seq., wherein the substituent R of the compounds of Formulas 1E, 1F, and 1I, or 2E, 2F, and 2I, is C$_{1-4}$alkyl (e.g., methyl).

5.5 Method 1I or 2I, or any of 5.1 et seq., wherein the substituent R of the compounds of Formulas 1E, 1F and 1I, or 2E, 2F and 2I, is H.

5.6 Method 1I or 2I, or any of 5.1 et seq., wherein the protecting group B of the compounds of Formulas 1E and 1F, or 2E and 2F, is a group of the formula P-Z, wherein P is selected from CH$_2$, C(O), C(O)O and S(O)$_2$, and wherein Z is an optionally substituted alkyl, aryl, alkylaryl or —OR' wherein R' is alkyl, aryl, arylalkyl or heteroarylalkyl.

5.7 Method 5.6, wherein the protecting group B is an acyl group (e.g., an alkanoyl or alkoxycarbonyl group), for example, t-butoxycarbonyl, phenoxycarbonyl, ethoxycarbonyl, or methoxycarbonyl, or an optionally substituted benzyloxycarbonyl.

5.8 Method 5.7, wherein the protecting group B is ethoxycarbonyl.

5.9 Method 5.6, wherein the protecting group B is an optionally substituted benzyl group, e.g., benzyl, 4-methoxybenzyl, or 2,4-dimethoxybenzyl.

5.10 Method 1I or 2I, or any of 5.1 et seq., wherein the transition metal catalyst of step (a) is a copper catalyst.

5.11 Method 5.10, wherein the transition metal catalyst of step (a) is selected from CuI, CuBr, CuCl, Cu(OAc)$_2$, Cu$_2$Cl$_2$, CuBr$_2$, CuSO$_4$, Cu$_2$SO$_4$, and Cu$_2$O.

5.12 Method 5.11, wherein the transition metal catalyst of step (a) is selected from CuI, CuBr and CuCl.

5.13 Method 5.12 wherein the transition metal catalyst is CuI.

5.14 Method 1I or 2I, or any of 5.1 et seq., wherein the transition metal catalyst of step (a) is present in an amount of 0.01 to 0.50 equivalents, e.g., from 0.05 to 0.40 equivalents, or from 0.10 to 0.30 equivalents, or from 0.15 to 0.25 equivalents, or about 0.20 equivalents.

5.15 Method 1I or 2I, or any of 5.1 et seq., wherein the base of step (a) is a Bronsted base, for example, selected from amines, alkoxides, carbonates and phosphates, and mixtures thereof 5.16 Method 5.15, wherein the base of step (a) is a carbonate base, for example, an alkali or alkaline earth metal carbonate or bicarbonate, or mixtures thereof 5.17 Method 5.16, wherein the base of step (a) is selected from sodium carbonate, potassium carbonate, sodium bicarbonate, or potassium bicarbonate, or a mixture thereof.

5.18 Method 5.17, wherein the base of step (a) comprises potassium carbonate, optionally in an amount of 1.5 to 3 equivalents, e.g., 2 to 2.5 equivalents, or about 2.2 equivalents.

5.19 Method 1I or 2I, or any of 5.1 et seq., wherein step (a) does not comprise the base (ii), e.g., does not comprise an alkoxide, carbonate, phosphate or other inorganic base.

5.20 Method 1I or 2I, or any of 5.1 et seq., wherein step (a) comprises an alkali metal or ammonium iodide or bromide, e.g., selected from sodium iodide, potassium iodide, lithium iodide, sodium bromide, potassium bromide, lithium bromide, or a tetraalkylammonium bromide or iodide (e.g., tetrabutylammonium bromide or iodide).

5.21 Method 5.20, wherein step (a) comprises potassium iodide.

5.22 Method 1I or 2I, or any of 5.1 et seq., wherein step (a) comprises a mono-dentate or bi-dentate ligand, for example, a ligand selected from phenolic or amine ligands.

5.23 Method 5.22, wherein the ligand is selected from an optionally substituted 1,2-diamine, an optionally substituted 1,2-aminoalcohol, DBU, DBN, or DABCO.

5.24 Method 5.23, wherein the ligand is DBU.

5.25 Method 1I or 2I, or any of 5.1 et seq., wherein the ligand of step (a) is present in an amount of 0.01 to 0.50 equivalents, e.g., from 0.05 to 0.45 equivalents, or from 0.10 to 0.40 equivalents, or from 0.20 to 0.30 equivalents, or about 0.25 equivalents.

5.26 Method 1I or 2I, or any of 5.1 et seq., wherein the solvent for step (a) is dioxane or toluene.

5.27 Method 5.26, wherein the solvent for step (a) is toluene.

5.28 Method 5.27, wherein the Compound of Formula 1E or 2E is combined with the base (ii) in toluene solvent and the mixture is azeotropically distilled to remove water prior to addition of the catalyst (i) and the optional iodide (iii) and/or the optional ligand (iv).

5.29 Method 1I or 2I, or any of 5.1 et seq., wherein the Compound of Formula 1F or 2F is isolated by cooling the reaction mixture to room temperature and then diluting the mixture with a non-polar solvent (e.g., pentanes, n-pentane, hexanes, n-hexane, heptanes, n-heptane, cyclopentane, cyclohexane, or a combination thereof) to precipitate the product, followed by filtration to isolate the precipitate.

5.30 Method 5.29, wherein the reaction solvent is toluene and the added non-polar solvent is a heptane (e.g., heptanes or n-heptane).

5.31 Method 5.29 or 5.30, wherein the precipitated solid (e.g., filter cake) is slurried with aqueous inorganic base (e.g., aqueous NaOH, KOH or $NH_4OH$) followed by filtration and washing with water.

5.32 Method 1I or 2I, or any of 5.1 et seq., wherein the deprotection step (b) is an acid- or base-mediated cleavage reaction, a hydrolysis reaction (e.g., acid- or base-catalysed) or hydrogenation reaction.

5.33 Method 5.32, wherein the deprotection step (b) is an acidic hydrolysis, e.g., an aqueous or non-aqueous acidic hydrolysis.

5.34 Method 5.33, wherein the acidic hydrolysis comprises an acid, e.g., selected from hydrochloric acid, hydrobromic acid, sulfuric acid, phosphoric acid, and nitric acid, optionally an excess of acid (e.g., 10-30 molar equivalents of acid).

5.35 Method 5.33, wherein the acidic hydrolysis comprises the acid in a non-aqueous solvent, e.g., acetic acid, ether or THF.

5.36 Method 5.33, wherein the acidic hydrolysis comprises the acid in an aqueous solvent, e.g., water or a water-alcohol mixture (e.g., water-methanol, or water-ethanol).

5.37 Method 5.35, wherein the deprotection step (b) comprises use of hydrobromic acid in acetic acid (e.g., 33% w/w HBr in AcOH).

5.38 Any of Methods 5.32-5.37, wherein the deprotection step comprises the use of hydrobromic acid or hydrogen bromide and the step further comprises washing the initial or final product with a polar solvent (e.g., ethyl acetate, methyl tert-butyl ether, acetonitrile, tetrahydrofuran, 1,4-dioxane, or combinations thereof, or one or more thereof sequentially) to remove bromine from the product.

5.39 Any of Methods 5.32-5.38, wherein step (b) initially yields an acid-addition salt form of the compound of Formula 1I or 2I (e.g., an HCl or HBr salt), and wherein step (b) further comprises a neutralization step to convert the acid addition salt form of the compound of Formula 1I or 2I to the corresponding free-base form.

5.40 Method 5.39, wherein the neutralization step comprises combining the acid addition salt form of the compound of Formula 1I or 2I with an inorganic base (e.g., an ammonium, alkali metal or alkaline earth metal hydroxide, alkoxide, carbonate or bicarbonate).

5.41 Method 5.40, wherein the inorganic base is ammonium hydroxide, optionally in the form of aqueous ammonia (e.g., 25% w/v aqueous ammonia).

5.42 Method 5.32, wherein the deprotection step (b) is a base-mediated cleavage, e.g., comprising an organic base (e.g. piperidine) in an organic solvent.

5.43 Method 5.32, wherein the deprotection step (b) is a hydrogenation reaction, e.g., a catalytic hydrogen comprising a transition metal catalyst (e.g., platinum or palladium) and hydrogen.

5.44 Method 1I or 2I, or any of 5.1 et seq., wherein the compound of Formula 1I or 2I (e.g., the compound of any of 1.1-1.8 or 2.1-2.8) is obtained as a solid, e.g., as an amorphous or crystalline solid (either in free base or acid addition salt form).

5.45 Method 1I or 2I, or any of 5.1 et seq., wherein the compound of Formula 1I or 2I (e.g., the compound of any of 1.1-1.8 or 2.1-2.8) is obtained in substantially pure form, e.g., greater than 90 wt % pure, or, e.g., greater than 95 wt % pure, up to 100 wt % pure.

5.46 Method 1I or 2I, or any of 5.1 et seq., wherein the compound of Formula 1I or 2I (e.g., the compound of any of 1.1-1.8 or 2.1-2.8) is obtained in free form (i.e., free base form), optionally as a crystalline solid.

5.47 Method 1I or 2I, or any of 5.1 et seq., wherein the compound of Formula 1I or 2I (e.g., the compound of any of 1.1-1.8 or 2.1-2.8) is obtained in salt form, e.g., acid addition salt form.

5.48 Method 5.47, wherein the compound of Formula 1I or 2I (e.g., the compound of any of 1.1-1.8 or 2.1-2.8) is obtained as an addition salt selected from a hydrochloride, hydrobromide, hydroiodide, formate, acetate, trifluoroacetate or methanesulfonate, e.g. in a base to acid molar ratio of 1:1 to 2:1.

5.49 Method 5.48, wherein the compound of Formula 1I or 2I (e.g., the compound of any of 1.1-1.8 or 2.1-2.8) is obtained as a hydrochloride or hydrobromide salt, e.g., as a solid hydrochloride or hydrobromide salt or crystalline solid hydrochloride or hydrobromide salt.

5.50 Method 1I or 2I, or any of 5.1 et seq., wherein the method takes place without isolation or without purification of the intermediate of the Formula 1F or 2F.

5.51 Method 1I or 2I, or any of 5.1 et seq., wherein steps (a) and (b) take place sequentially in a single reaction vessel or set of connected reaction vessels.

5.52 Method 1I or 2I, or any of 5.1 et seq., wherein the compound of Formula 1I or 2I (e.g., the compound of any of 1.1-1.8 or 2.1-2.8) is obtained in a form having less than about 50 ppm of copper, or less than about 10 ppm of copper, or less than about 5 ppm of copper.

5.53 Method 1I or 2I, or any of 5.1 et seq., wherein the method further comprises a step (c) of alkylating the piperidine nitrogen of the compound of Formula 1I or 2I with a suitable alkylating agent, as herein described, to yield a compound of Formula 1J or 2J, in free or salt form.

5.54 Method 5.53, wherein the compound of Formula 1J or 2J is obtained in free base form from step (c), and wherein the method further comprises a step (d) of converting said compound of Formula 1J or 2J in free base form into a compound of Formula 1J or 2J in salt form, e.g., acid addition salt form (e.g., tosylate salt form).

5.55 Method 5.53 or 5.54 wherein the method provides a compound of Formula 1J or 2J as described by Formulas 3.1-3.12 or 4.1-4.12, respectively.

5.56 Method 1I or 2I, or any of 5.1 to 5.55, further comprising any or all of the following steps as described in any embodiments thereof herein throughout:
  a. Preparing the compound of Formula 1A by reacting 2-bromophenylhydrazine, in free or salt form, with 4-piperidinone, in free or salt form, optionally in hydrate form, optionally in acetic acid solvent;
  b. Preparing the compound of Formula 1C or 2C, in free or salt form, by (a) reducing the compound of Formula 1A to a compound of Formula 1B, optionally wherein the reduction comprises reaction of the compound of Formula 1A with triethylsilane and methanesulfonic acid, and (b) separating the stereoisomers of Formula 1B by chiral salt resolution or chiral chromatography to yield the compound of Formula 1C or 2C, optionally wherein the chiral salt resolution is performed in a single resolution step using S-mandelic acid;
  c. Preparing the compound of Formula 1D or 2D, in free or salt form, by protecting the piperidine amine of the compound of Formula 1C or 2C with a protecting agent in the presence of a base;
  d. Preparing the compound of Formula 1E or 2E, in free or salt form, by N-alkylating a compound of Formula 1D or 2D with (a) a nucleophilic alkyl halide, and (b) a base.

In another aspect, the invention provides a method (Method 1J) for preparing a compound of Formula 1J, or any of 3.1-3.12, in free or salt form, comprising the steps of (a) reacting a compound of Formula 1E, in free or salt form, with (i) a transition metal catalyst selected from the group consisting of Groups 8-11 of the periodic table, (ii) optionally a base, (iii) optionally an alkali metal or ammonium iodide or bromide (e.g. potassium iodide or tetrabutylammonium bromide), and (iv) optionally a monodentate or bidentate ligand, to form an intermediate of Formula 1F, in free or salt form; (c) deprotecting the piperidine nitrogen of the compound of Formula 1F to yield the compound of Formula 1I (or any of 1.1-1.8), in free or salt form; and (c) alkylating the piperidine nitrogen of the compound of Formula 1I with a suitable alkylating agent to yield the compound of Formula 1J (or any of 3.1-3.12) in free or salt form; and optionally (d) converting the compound of Formula 1J in free form to a compound of Formula 1J (or any of 3.1-3.12) in salt form, e.g., pharmaceutically acceptable salt form, such as acid addition salt form (e.g., tosylate salt form). In some embodiments, the method further comprises the step of alkylating a compound of Formula 1D to form the compound of Formula 1E.

In another embodiment of the second aspect, the invention provides a method (Method 2J) for preparing a compound of Formula 2J, or any of 4.1-4.15, in free or salt form, comprising the steps of (a) reacting a compound of Formula 2E, in free or salt form, with (i) a transition metal catalyst selected from the group consisting of Groups 8-11 of the periodic table, (ii) optionally a base, (iii) optionally an alkali metal or ammonium iodide or bromide (e.g. potassium iodide or tetrabutylammonium bromide), and (iv) optionally a monodentate or bidentate ligand, to form an intermediate of Formula 2F, in free or salt form; (b) deprotecting the piperidine nitrogen of the compound of Formula 2F to yield the compound of Formula 2I (or any of 2.1-2.8), in free or salt form; and (c) alkylating the piperidine nitrogen of the compound of Formula 1I with a suitable alkylating agent to yield the compound of Formula 2J (or any of 4.1-4.12) in free or salt form; and optionally (d) converting the compound of Formula 2J in free form to a compound of Formula 2J (or any of 4.1-4.12) in salt form, e.g., pharmaceutically acceptable salt form, such as acid addition salt form (e.g., tosylate salt form). In some embodiments, the method further comprises the step of alkylating a compound of Formula 2D to form the compound of Formula 2E.

In all respects, steps (a) and (b) of Method 1J and 2J may be carried according to the description above for Method 1I and 2I, respectively, including any of Methods 5.1-5.56.

Alkylating agents suitable for step (c) of Method 1J or 2J include compounds of the general formula Q-X, wherein Q is selected from 4-(4-fluorophenyl)-4-oxobutyl and 3-(4-fluorophenoxy)propyl, and wherein X is any suitable leaving group. Leaving groups are entities known in the art to be amenable to nucleophilic substitution reactions. In some embodiments, X is selected from chloro, bromo, iodo, $C_{1-4}$alkylsulfonyloxy (e.g. methanesulfonyloxy) and optionally substituted arylsulfonyloxy (e.g., benzenesulfonyloxy, 4-nitrobenzenesulfonyloxy, 4-halosulfonyloxy, and the like).

In some embodiments, step (c) of Method 1J or 2J, may further comprise a suitable base. Suitable bases include, but are not limited to, organic bases such as amine bases (e.g., ammonia, triethylamine, N,N'-diisopropylethylamine or 4-(dimethylamino)pyridine (DMAP), 1,5-diazabicycl[4.3.0]-non-5-ene (DBN), 1,5-diazabicyclo[5.4.0]undec-5-ene (DBU)); or inorganic bases such as hydrides (e.g. sodium, lithium or potassium hydride), alkoxides (e.g. sodium, potassium or lithium t-butoxide), aryloxides (e.g., lithium, sodium or potassium phenoxide), or carbonates, bicarbonates, phosphates or hydroxides of alkali or alkaline earth metals (e.g. sodium, magnesium, calcium, potassium, cesium or barium carbonate, bicarbonate, hydroxide or phosphate). Optionally, step (c) may further comprise an inorganic iodide salt, such as potassium iodide or sodium iodide, preferably potassium iodide. Suitable solvents include polar protic and/or polar aprotic solvents, such as, acetonitrile, dioxane, dimethylformamide, dimethylacetamide, dimethylsulfoxide, methanol, ethanol, isopropanol, and mixtures thereof. In a preferred embodiment, step (c) comprises reaction of the compound of Formula 1I or 2I with the alkylating agent 1-chloro-3-(4-fluorophenoxy)propane, and a base selected from triethylamine, diisopropylethylamine, potassium carbonate and sodium carbonate. Where a base is used, the amount of base can be any amount from a catalytic amount (e.g., 0.01 equivalents) to an excess amount (e.g., 10 or more equivalents). In some embodiments, the reaction is performed with from 1.0 to 10.0 equivalents of base, e.g., 3.0 to 10.0 or 4.0 to 6.0 equivalents of base.

The compound of Formula 1J or 2J, which results from step (c) of Method 1J or 2J, may be obtained as a free base or as a salt. Suitable salt forms include acid addition salts, such as phosphates, sulfates, hydrohalides (e.g., hydrochloride), and carboxylates (e.g., acetate or formate). Either the free base form or a salt form of the compound of Formula 1J or 2J may be obtained, e.g., isolated or purified, by any suitable method. In some embodiments, the reaction of step (c) is performed in the presence of an excess of base, and this may permit the isolation of the free base for of the compound of Formula 1J or 2J from the reaction mixture (e.g., by aqueous/organic extraction, and/or by chromatography, and/or by precipitation from a suitable solvent, and/or by evaporation of the reaction solvent). In some embodiments, the reaction of step (c) is performed in the absence of base or in the presence of less than one equivalent of base (e.g., 0.5 equivalent or less, or a catalytic amount). Particularly when performed in the absence of base, step (c) may yield an acid addition salt of the compound of Formula 1J or 2J, wherein the acid component of the salt is derived from the alkylating agent. For example, if the compound of Formula 1I or 2I is treated with an alkylating agent Q-X, as defined above, and in the absence of an added base, the resulting compound of Formula 1J or 2J may be obtained as the acid addition salt corresponding to the group X (e.g., if X is chloro, then the compound of Formula 1J or 2J may be obtained in the form of a hydrochloride acid addition salt). In some embodiments, an equimolar or only moderate excess of base is used during the reaction of step (c), but prior to or during purification, an excess of acid (e.g., hydrochloric acid) is added, resulting in obtainment of the compound of Formula 1J or 2J as an acid addition salt (e.g. hydrochloride).

In some embodiments, step (c) of Method 1J or 2J yields the compound of Formula 1J or 2J in free form (i.e., free base form), and this form is isolated and/or purified, and then, optionally, step (d) is performed to convert the free base form of said compound of Formula 1J or 2J into a salt form of said compound of Formula 1J or 2J, for example, a pharmaceutically acceptable salt form (e.g., an acid addition salt). In some embodiments, this acid addition salt form of said compound of Formula 1J or 2J is further isolated and/or purified. Without being bound by theory, it is believed that the initial isolation of the compound of Formula 1J or 2J in free form, followed by subsequent conversion of this compound into salt form (e.g., acid addition salt form) results in a final product (compound of Formula 1J or 2J) of higher purity and/or workability.

Step (d) of Method 1J or 2J may be carried out by reacting the free base form of the compound of Formula 1J or 2J with an appropriate acid, in water or in an organic solvent, or in a mixture of the two, to give, for example, a pharmaceutically acceptable acid addition salt of Formula 1J or 2J of the present invention. Appropriate acids are generally known in the art, and may include, for example, hydrochloric acid or toluenesulfonic acid. When a monovalent acid is used (e.g., hydrochloric acid or toluenesulfonic acid), step (d) may result in a mono-addition salt or a di-addition salt, depending on the molar equivalent of acid to free base used (e.g., from 1:1 free base to acid to 1:2 free base to acid).

In specific embodiments of this aspect, the present disclosure provides:

6.1 Method 1J or 2J, wherein the compound of Formula 1I or 2I is, respectively, a compound according to any of Formula 1.1-1.8 or 2.1-2.8.

6.2 Method 1J or 2J, wherein the substituent A of the compound of Formula 1E or 2E is selected from Br, Cl and I.

6.3 Method 6.2, wherein A is Br.

6.4 Method 1J or 2J, or any of 6.1 et seq., wherein the substituent R of the compounds of Formulas 1E, 1F, and 1I, or 2E, 2F, and 2I, is $C_{1-4}$alkyl (e.g., methyl).

6.5 Method 1J or 2J, or any of 6.1 et seq., wherein the substituent R of the compounds of Formulas 1E, 1F and 1I, or 2E, 2F and 2I, is H.

6.6 Method 1J or 2J, or any of 6.1 et seq., wherein the protecting group B of the compounds of Formulas 1E and 1F, or 2E and 2F, is a group of the formula P-Z, wherein P is selected from $CH_2$, $C(O)$, $C(O)O$ and $S(O)_2$, and wherein Z is an optionally substituted alkyl, aryl, alkylaryl or —OR' wherein R' is alkyl, aryl, arylalkyl or heteroarylalkyl.

6.7 Method 6.6, wherein the protecting group B is an acyl group (e.g., an alkanoyl or alkoxycarbonyl group), for example, t-butoxycarbonyl, phenoxycarbonyl, ethoxycarbonyl, or methoxycarbonyl, or an optionally substituted benzyloxycarbonyl.

6.8 Method 6.7, wherein the protecting group B is ethoxycarbonyl.

6.9 Method 6.6, wherein the protecting group B is an optionally substituted benzyl group, e.g., benzyl, 4-methoxybenzyl, or 2,4-dimethoxybenzyl.

6.10 Method 1J or 2J, or any of 6.1 et seq., wherein the transition metal catalyst of step (a) is a copper catalyst.

6.11 Method 6.10, wherein the transition metal catalyst of step (a) is selected from CuI, CuBr, CuCl, $Cu(OAc)_2$, $Cu_2Cl_2$, $CuBr_2$, $CuSO_4$, $Cu_2SO_4$, and $Cu_2O$.

6.12 Method 6.11, wherein the transition metal catalyst of step (a) is selected from CuI, CuBr and CuCl.

6.13 Method 6.12 wherein the transition metal catalyst is CuI.

6.14 Method 1J or 2J, or any of 6.1 et seq., wherein the transition metal catalyst of step (a) is present in an amount of 0.01 to 0.50 equivalents, e.g., from 0.05 to 0.40 equivalents, or from 0.10 to 0.30 equivalents, or from 0.15 to 0.25 equivalents, or about 0.20 equivalents.

6.15 Method 1J or 2J, or any of 6.1 et seq., wherein the base of step (a) is a Bronsted base, for example, selected from amine bases, alkoxides, carbonates and phosphates, and mixtures thereof 6.16 Method 6.15, wherein the base of step (a) is a carbonate base, for example, an alkali or alkaline earth metal carbonate or bicarbonate, or mixtures thereof 6.17 Method 6.16, wherein the base of step (a) is selected from sodium carbonate, potassium carbonate, sodium bicarbonate, or potassium bicarbonate, or a mixture thereof.

6.18 Method 6.17, wherein the base of step (a) comprises potassium carbonate, optionally in an amount of 1.5 to 3 equivalents, e.g., 2 to 2.5 equivalents, or about 2.2 equivalents.

6.19 Method 1J or 2J, or any of 6.1 et seq., wherein step (a) does not comprise the base (ii), e.g., does not comprise an alkoxide, carbonate, phosphate or other inorganic base.

6.20 Method 1J or 2J, or any of 6.1 et seq., wherein step (a) comprises an alkali metal or ammonium iodide or bromide, e.g., selected from sodium iodide, potassium iodide, lithium iodide, sodium bromide, potassium bromide, or lithium bromide, or a tetraalkylammonium bromide or iodide (e.g., tetrabutylammonium bromide or iodide).

6.21 Method 6.20, wherein step (a) comprises potassium iodide.

6.22 Method 1J or 2J, or any of 6.1 et seq., wherein step (a) comprises a mono-dentate or bi-dentate ligand, for example, a ligand selected from phenolic or amine ligands.

6.23 Method 6.22, wherein the ligand is selected from an optionally substituted 1,2-diamine, an optionally substituted 1,2-aminoalcohol, DBU, DBN, or DABCO.

6.24 Method 6.23, wherein the ligand is DBU.

6.25 Method 1J or 2J, or any of 6.1 et seq., wherein the ligand of step (a) is present in an amount of 0.01 to 0.50 equivalents, e.g., from 0.05 to 0.45 equivalents, or from 0.10 to 0.40 equivalents, or from 0.20 to 0.30 equivalents, or about 0.25 equivalents.

6.26 Method 1J or 2J, or any of 6.1 et seq., wherein the solvent for step (a) is dioxane or toluene.

6.27 Method 6.26, wherein the solvent for step (a) is toluene.

6.28 Method 6.27, wherein the Compound of Formula 1E or 2E is combined with the base (ii) in toluene solvent and the mixture is azeotropically distilled to remove water prior to addition of the catalyst (i) and the optional iodide (iii) and/or the optional ligand (iv).

6.29 Method 1J or 2J, or any of 6.1 et seq., wherein the Compound of Formula 1F or 2F is isolated by cooling the reaction mixture to room temperature and then diluting the mixture with a non-polar solvent (e.g., pentanes, n-pentane, hexanes, n-hexane, heptanes, n-heptane, cyclopentane, cyclohexane, or a combination thereof) to precipitate the product, followed by filtration to isolate the precipitate.

6.30 Method 6.29, wherein the reaction solvent is toluene and the added non-polar solvent is a heptane (e.g., heptanes or n-heptane).

6.31 Method 6.29 or 6.30, wherein the precipitated solid (e.g., filter cake) is slurried with aqueous inorganic base (e.g., aqueous NaOH, KOH or NH$_4$OH) followed by filtration and washing with water.

6.32 Method 1J or 2J, or any of 6.1 et seq., wherein the deprotection step (b) is an acid- or base-mediated cleavage reaction, a hydrolysis reaction (e.g., acid- or base-catalysed) or hydrogenation reaction.

6.33 Method 6.32, wherein the deprotection step (b) is an acidic hydrolysis, e.g., an aqueous or non-aqueous acidic hydrolysis.

6.34 Method 6.33, wherein the acidic hydrolysis comprises an acidic catalyst, e.g., selected from hydrochloric acid, hydrobromic acid, sulfuric acid, phosphoric acid, and nitric acid, optionally an excess of acid (e.g., 10-30 molar equivalents of acid).

6.35 Method 6.33, wherein the acidic hydrolysis comprises the acid in a non-aqueous solvent, e.g., acetic acid, ether or THF.

6.36 Method 6.33, wherein the acidic hydrolysis comprises the acid in an aqueous solvent, e.g., water or a water-alcohol mixture (e.g., water-methanol, or water-ethanol).

6.37 Method 6.35, wherein the deprotection step (b) comprises use of hydrobromic acid in acetic acid (e.g., 33% w/w HBr in AcOH).

6.38 Any of Methods 6.32-6.37, wherein the deprotection step comprises the use of hydrobromic acid or hydrogen bromide and the step further comprises washing the initial or final product with a polar solvent (e.g., ethyl acetate, methyl tert-butyl ether, acetonitrile, tetrahydrofuran, 1,4-dioxane, or combinations thereof, or one or more thereof sequentially) to remove bromine from the product.

6.39 Any of Methods 6.32-6.38, wherein step (b) initially yields an acid-addition salt form of the compound of Formula 1I or 2I (e.g., an HCl or HBr salt), and wherein step (b) further comprises a neutralization step to convert the acid addition salt form of the compound of Formula 1I or 2I to the corresponding free-base form.

6.40 Method 6.39, wherein the neutralization step comprises combining the acid addition salt form of the compound of Formula 1I or 2I with an inorganic base (e.g., an ammonium, alkali metal or alkaline earth metal hydroxide, alkoxide, carbonate or bicarbonate).

6.41 Method 6.40, wherein the inorganic base is ammonium hydroxide, optionally in the form of aqueous ammonia (e.g., 25% w/v aqueous ammonia).

6.42 Method 6.32, wherein the deprotection step (b) is a base-mediated cleavage, e.g., comprising an organic base (e.g. piperidine) in an organic solvent.

6.43 Method 6.32, wherein the deprotection step (b) is a hydrogenation reaction, e.g., a catalytic hydrogen comprising a transition metal catalyst (e.g., platinum or palladium) and hydrogen.

6.44 Method 1J or 2J, or any of 6.1 et seq., wherein the compound of Formula 1I or 2I (e.g., the compound of any of 1.1-1.8 or 2.1-2.8) is obtained as a solid, e.g., as an amorphous or crystalline solid (either in free base or acid addition salt form).

6.45 Method 1J or 2J, or any of 6.1 et seq., wherein the compound of Formula 1I or 2I (e.g., the compound of any of 1.1-1.8 or 2.1-2.8) is obtained in substantially pure form, e.g., greater than 90 wt % pure, or, e.g., greater than 95 wt % pure, greater than 98.5% pure, up to 100 wt % pure.

6.46 Method 1J or 2J, or any of 6.1 et seq., wherein the compound of Formula 1I or 2I (e.g., the compound of any of 1.1-1.8 or 2.1-2.8) is obtained in free form (i.e., free base form), optionally as a crystalline solid.

6.47 Method 1J or 2J, or any of 6.1 et seq., wherein the compound of Formula 1I or 2I (e.g., the compound of any of 1.1-1.8 or 2.1-2.8) is obtained in salt form, e.g., acid addition salt form.

6.48 Method 6.48, wherein the compound of Formula 1I or 2I (e.g., the compound of any of 1.1-1.8 or 2.1-2.8) is obtained as an addition salt selected from a hydrochloride, hydrobromide, hydroiodide, formate, acetate, trifluoroacetate or methanesulfonate, e.g. in a base to acid molar ratio of 1:1 to 2:1.

6.49 Method 6.44, wherein the compound of Formula 1I or 2I (e.g., the compound of any of 1.1-1.8 or 2.1-2.8) is obtained as a hydrochloride or hydrobromide salt, e.g., as a solid hydrochloride or hydrobromide salt or crystalline solid hydrochloride or hydrobromide salt.

6.50 Method 1J or 2J, or any of 6.1 et seq., wherein the method takes place without isolation or without purification of the intermediate of the Formula 1F or 2F.

6.51 Method 1J or 2J, or any of 6.1 et seq., wherein steps (a) and (b) take place sequentially in a single reaction vessel or set of connected reaction vessels.

6.52 Method 1J or 2J, or any of 6.1 et seq., wherein the compound of Formula 1I or 2I (e.g., the compound of any of 1.1-1.8 or 2.1-2.8) is obtained in a form having less than about 50 ppm of copper, or less than about 10 ppm of copper, or less than about 5 ppm of copper.

6.53 Method 1J or 2J, or any of 6.1 et seq., wherein the compound of Formula 1J or 2J is, respectively, a compound of Formula 3.1-3.12 or 4.1-4.12.

6.54 Method 1J or 2J, or any of 6.1 et seq., wherein the suitable alkylating agent of step (c) is a compound of the general formula Q-X, wherein Q is selected from 4-(4-fluorophenyl)-4-oxobutyl and 3-(4-fluorophenoxy)propyl, and wherein X is any suitable leaving group (e.g., a functional group known in the art to be amenable to nucleophilic substitution reactions).

6.55 Method 6.50, wherein the group X is selected from chloro, bromo, iodo, $C_{1-4}$alkylsulfonyloxy (e.g. methanesulfonyloxy) and optionally substituted arylsulfonyloxy (e.g., benzenesulfonyloxy, 4-nitrobenzenesulfonyloxy, 4-halosulfonyloxy, and the like).

6.56 Method 1J or 2J, or any of 6.1 et seq., wherein the group Q of the compound of Formula 1J or 2J is 4-(4-fluorophenyl)-4-oxobutyl.

6.57 Method 1J or 2J, or any of 6.1 et seq., wherein the group Q of the compound of Formula 1J or 2J is 3-(4-fluorophenoxy)propyl.

6.58 Method 1J or 2J, or any of 6.1 et seq., wherein the alkylating agent is 4-chloro-4'-fluorobutyrophenone or 1-chloro-3-(4-fluorophenoxy)propane.

6.59 Method 1J or 2J, or any of 6.1 et seq., wherein step (c) comprises the alkylating agent (e.g., 1-chloro-3-(4-fluorophenoxy)propane) in an amount of 1 to 3 equivalents, e.g., 1 to 2 equivalents, or 1.25 to 1.75 equivalents or about 1.5 equivalents, for example, 1.35 to 1.65 equivalents.

6.60 Method 1J or 2J, or any of 6.1 et seq., wherein step (c) further comprises a suitable base, e.g., an organic base (e.g. an amine base) or an inorganic base (e.g., a hydride, alkoxide, aryloxide, carbonate, bicarbonate, phosphate or hydroxide base).

6.61 Method 6.56, wherein the base of step (c) is selected from triethylamine, diisopropylethylamine, sodium carbonate and potassium carbonate.

6.62 Method 6.57, wherein the base of step (c) is triethylamine or diisopropylethylamine.

6.63 Method 6.58, wherein the triethylamine or diisopropylethylamine is present in an amount of 1 to 10 equivalents, e.g., 2 to 10 equivalents, or 4 to 6 equivalents, or about 5 equivalents, for example, 4.5-5.5 equivalents.

6.64 Method 1J or 2J, or any of 6.1 et seq., wherein step (c) further comprises an inorganic iodide salt (e.g., potassium iodide or sodium iodide), optionally, in an amount of 0.75 to 1.5 equivalents, or 1 to 1.25 equivalents, or about 1 equivalent, for example, 0.9-1.1 equivalents.

6.65 Method 1J or 2J, or any of 6.1 et seq., wherein the solvent for step (d) is dimethylsulfoxide.

6.66 Method 1J or 2J, or any of 6.1 et seq., wherein the compound of Formula 1J or 2J is obtained in free base form from step (c).

6.67 Method 6.66, wherein the compound of Formula 1J or 2J in free base form is isolated from the reaction mixture by a process comprising the steps of (i) diluting the reaction mixture with an organic solvent (e.g., ethyl acetate) and water, (ii) separating the organic layer and concentrating it under vacuum to a low volume, and (iii) co-evaporating the residue with a nonpolar solvent (e.g., pentanes, n-pentane, hexanes, n-hexane, heptanes, n-heptane, cyclopentane, cyclohexane, or a combination thereof) from one to five times (e.g., three times) followed by collection of the solids by filtration.

6.68 Method 6.67, wherein the process for isolating the compound of Formula 1J or 2J comprises the step of precipitating the crude product from a suitable solvent (e.g., acetonitrile, acetone and/or methanol) to yield the free base solid (e.g., slurrying the crude product with said solvent and filtering to recover the product solid, and/or recrystallizing the product from said solvent).

6.69 Method 6.68, wherein the crude product is recrystallized from a binary solvent mixture, e.g., acetone-methanol or acetone-ethyl acetate, at a ratio between solvents of 5:1 to 1:5.

6.70 Method 6.69, wherein the recrystallization solvent is acetone-methanol in a ratio of 2:1 to 4:1 acetone to methanol, e.g., 3:1 acetone to methanol.

6.71 Any of methods 6.68-6.70, wherein the method comprises slurrying the crude product with acetonitrile followed by recrystallization with a binary solvent (e.g., acetone-methanol).

6.72 Method 1J or 2J, or any of 6.1 et seq., wherein the compound of Formula 1J or 2J is obtained in the form of a salt from step (c), e.g., an acid addition salt (e.g., a hydrochloride salt).

6.73 Any of Methods 6.66-6.71, wherein the compound of Formula 1J or 2J is obtained in free base form from step (c), and wherein the method further comprises a step (d) of converting said compound of Formula 1J or 2J in free base form into a compound of Formula 1J or 2J in salt form, e.g., acid addition salt form (e.g., a tosylate salt form).

6.74 Method 6.73, wherein step (d) comprises treating the compound of Formula 1J or 2J in free base form with an acid (e.g., toluenesulfonic acid) in an amount of 1.25 to 2.00 molar equivalents of acid compared the free base (e.g., 1.3 to 1.6 equivalents, or about 1.5 equivalents), in a suitable solvent (e.g., methanol, ethanol, propanol, isopropanol, acetonitrile, methyl isobutyl ketone, methyl ethyl ketone).

6.75 Method 6.73 or 6.74, wherein the temperature of step (d) is from 25° C. to 100° C., e.g., from 30° C. to 60° C., or from 45° C. to 55° C., or 50° C.

6.76 Method 6.74 or 6.75, wherein the acid is toluenesulfonic acid and the solvent is methyl ethyl ketone.

6.77 Any of methods 6.73-6.76, wherein step (d) results in spontaneous precipitation of the compound of Formula 1J or 2J in solid form, optionally in crystalline form, optionally followed by washing with a solvent (e.g., the salt formation solvent).

6.78 Method 1J or 2J, or any of 6.1 et seq., wherein the method provides the compound of Formula 1J or 2J in free base form, optionally in solid crystalline free base form.

6.79 Method 1J or 2J, or any of 6.1 et seq., wherein the method provides the compound of Formula 1J or 2J in acid addition salt form, optionally in solid crystalline salt form.

6.80 Method 6.79, wherein the acid addition salt form is a tosylate salt form.

6.81 Method 1J or 2J, or any of 6.1 et seq., wherein the method provides the compound of Formula 1J or 2J in at least 70%, preferably at least 80%, more preferably at least 90%, most preferably greater than 95%, up to 100%, cis stereoisomer relative to all other stereoisomers.

6.82 Method 1J or 2J, or any of 6.1 et seq., wherein the method provides the compound of Formula 1J or 2J in substantially enantiomerically pure form, e.g., in at least 90% e.e., preferably in at least 95% e.e., or in at least 97% e.e, or in at least 99% e.e., or at least 99.5% e.e., or in at least 99.9% e.e., up to 100% e.e.

6.83 Method 1J or 2J, or any of 6.1 et seq., wherein the method provides the compound of Formula 1J or 2J in substantially pure form, e.g., as measured by HPLC, for example greater than 95% pure form, or greater than 97%, greater than 98%, greater than 98.5%, greater than 99%, greater than 99.5% or greater than 99.9% pure form, up to 100% pure form.

6.84 Method 1J or 2J, or any of 6.1 et seq., wherein the method provides the compound of Formula 1J or 2J in a form having less than about 50 ppm of copper, or less than about 10 ppm of copper, or less than about 5 ppm of copper.

6.85 Method 1J or 2J, or any of 6.1 to 6.84, wherein the method provides the compound of Formula 1J or 2J in admixture with at least 0.001% by weight and less than 2% by weight of at least one compound selected from the compound of Formula 1K or 2K, or 1L or 2L.

6.86 Method 6.85, wherein the method provides the compound of Formula 1J or 2J in admixture with at least 0.10% by weight and less than 2% by weight of at least one compound selected from the compound of Formula 1K or 2K, or 1L or 2L.

6.87 Method 6.86, wherein the method provides the compound of Formula 1J or 2J in admixture with at least 1.0% by weight and less than 2.0% by weight of the compound of Formula 1K or 2K.

6.88 Method 6.86 or 6.87, wherein the method provides the compound of Formula 1J or 2J in admixture with at least 1.0% by weight and less than 2.0% by weight of the compound of Formula 1L or 2L.

6.89 Method 1J or 2J, or any of 6.1 et seq., wherein the method provides the compound of Formula 1J or 2J in admixture with less than 1.0% by weight of 1-chloro-3-(4-fluorophenoxy)propane), e.g., less than 0.5%, or less than 0.25%, or less than 0.15% or less than 0.10%, or less than 0.08% by weight of 1-chloro-3-(4-fluorophenoxy)propane).

6.90 Method 1J or 2J, or any of 6.1 et seq., wherein the method provides the compound of Formula 1J or 2J in admixture with less than 5000 ppm of any organic solvent (e.g., acetone, acetonitrile or methanol), e.g., less than 4000 ppm, or less than 3000 ppm, or less than 1500 ppm, or less than 1000 ppm, or less than 500 ppm, or less than 410 ppm, of any such organic solvent.

6.91 Any of methods 6.85-6.90, wherein in the compound of Formula 1K or 2K, or 1L or 2L, the group R is H and the group Q is —O—.

6.92 Method 1J or 2J, or any of 6.1 to 6.91, further comprising any or all of the following steps as described in any embodiments thereof herein throughout:
a. Preparing the compound of Formula 1A by reacting 2-bromophenylhydrazine, in free or salt form, with 4-piperidinone, in free or salt form, optionally in hydrate form, optionally in acetic acid solvent;
b. Preparing the compound of Formula 1C or 2C, in free or salt form, by (a) reducing the compound of Formula 1A to a compound of Formula 1B, optionally wherein the reduction comprises reaction of the compound of Formula 1A with triethylsilane and methanesulfonic acid, and (b) separating the stereoisomers of Formula 1B by chiral salt resolution or chiral chromatography to yield the compound of Formula 1C or 2C, optionally wherein the chiral salt resolution is performed in a single resolution step using S-mandelic acid;
c. Preparing the compound of Formula 1D or 2D, in free or salt form, by protecting the piperidine amine of the compound of Formula 1C or 2C with a protecting agent in the presence of a base;
d. Preparing the compound of Formula 1E or 2E, in free or salt form, by N-alkylating a compound of Formula 1D or 2D with (a) a nucleophilic alkyl halide, and (b) a base.

In another aspect, the invention provides a method (Method 1F) for preparing a compound of Formula 1F, in free or salt form, comprising the steps of (a) reacting a compound of Formula 1E, in free or salt form, in a solvent comprising toluene, with (i) a transition metal catalyst selected from the group consisting of Groups 8-11 of the periodic table, (ii) a base, (iii) optionally an alkali metal or ammonium iodide or bromide (e.g. potassium iodide or tetrabutylammonium bromide), and (iv) one or more mono- or bi-dentate ligands comprising DBU, to form the compound of Formula 1F, in free or salt form, followed by (b) isolating the compound of Formula 1F, in free or salt form, by precipitation from a hydrophobic solvent mixture.

In another embodiment of the this aspect, the invention provides a method (Method 2F) for preparing a compound of Formula 2F in free or salt form, comprising the steps of (a) reacting a compound of Formula 2E, in free or salt form, in a solvent comprising toluene, with (i) a transition metal catalyst selected from the group consisting of Groups 8-11 of the periodic table, (ii) a base, (iii) optionally an alkali metal or ammonium iodide or bromide (e.g. potassium iodide or tetrabutylammonium bromide), and (iv) one or more mono- or bi-dentate ligands comprising DBU, to form the compound of Formula 2F, in free or salt form, followed by (b) isolating the compound of Formula 2F, in free or salt form, by precipitation from a hydrophobic solvent mixture.

Prior art methods for the synthesis of compounds such as those of Formula 1F or 2F involved the use of copper iodide, in dioxane solvent with the ligand N,N,N',N'-tetramethylethylenediamine, or the use of copper iodide in toluene solvent with potassium carbonate base and DBU ligand. However, these prior art methods suffered from one or more of (1) long reaction times, (2) the formation of undesirable impurities, and/or (3) loss of product to decomposition during evaporation of reaction solvent. Applicant has unexpectedly found that the choice of reaction and purification conditions are critical to improving yield. In particular, it was unexpectedly found that water promotes the formation of impurities and decomposition. The use of toluene as solvent, especially azeotropically distilled toluene, results in improved product yield and purity. In addition, it was unexpectedly found that the precipitation of the product from the reaction mixture induced by the addition of hydrophobic hydrocarbon solvent provides a purer and higher yielding product, compared to prior art methods.

In particular embodiments of Methods 1F and 2F, the present disclosure further provides:

7.1 Method 1F or 2F, wherein the transition metal catalyst of step (a) is a copper catalyst.

7.2 Method 7.1, wherein the transition metal catalyst of step (a) is selected from CuI, CuBr, CuCl, Cu(OAc)$_2$, Cu$_2$Cl$_2$, CuBr$_2$, CuSO$_4$, Cu$_2$SO$_4$, and Cu$_2$O.

7.3 Method 7.2, wherein the transition metal catalyst of step (a) is selected from CuI, CuBr and CuCl.

7.4 Method 7.3, wherein the transition metal catalyst is CuI.

7.5 Method 1F or 2F, or any of 7.1 et seq., wherein the transition metal catalyst of step (a) is present in an amount of 0.01 to 0.50 equivalents, e.g., from 0.05 to 0.40 equivalents, or from 0.10 to 0.30 equivalents, or from 0.15 to 0.25 equivalents, or about 0.20 equivalents.

7.6 Method 1F or 2F, or any of 7.1 et seq., wherein the base of step (a) is a Bronsted base, for example, selected from amine bases, alkoxides, carbonates and phosphates, and mixtures thereof 7.7 Method 7.6, wherein the base of step (a) is a carbonate base, for example, an alkali or alkaline earth metal carbonate or bicarbonate, or mixtures thereof 7.8 Method 7.7, wherein the base of step (a) is selected from sodium carbonate, potassium carbonate, sodium bicarbonate, or potassium bicarbonate, or a mixture thereof.

7.9 Method 7.8, wherein the base of step (a) comprises potassium carbonate, optionally in an amount of 1.5 to 3 equivalents, e.g., 2 to 2.5 equivalents, or about 2.2 equivalents.

7.10 Method 1F or 2F, or any of 7.1 et seq., wherein step (a) comprises an alkali metal or ammonium iodide or bromide, e.g., selected from sodium iodide, potassium iodide, lithium iodide, sodium bromide, potassium bromide, lithium bromide, or a tetraalkylammonium iodide or bromide (e.g., tetrabutylammonium bromide).

7.11 Method 7.10, wherein step (a) comprises potassium iodide.

7.12 Method 1F or 2F, or any of 7.1 et seq., wherein the DBU ligand of step (a) is present in an amount of 0.01 to 0.50 equivalents, e.g., from 0.05 to 0.45 equivalents, or from 0.10 to 0.40 equivalents, or from 0.20 to 0.30 equivalents, or about 0.25 equivalents.

7.13 Method 1F or 2F, or any of 7.1 et seq., wherein the Compound of Formula 1E or 2E is combined with the base (ii) in toluene solvent and the mixture is azeotropically distilled to remove water prior to addition of the catalyst (i) and the optional iodide (iii) and the ligand (iv).

7.14 Method 1F or 2F, or any of 7.1 et seq., wherein the Compound of Formula 1F or 2F is isolated by cooling the reaction mixture to room temperature and then diluting the mixture with a non-polar solvent (e.g., pentanes, n-pentane, hexanes, n-hexane, heptanes, n-heptane, cyclopentane, cyclohexane, or a combination thereof) to precipitate the product, followed by filtration to isolate the precipitate.

7.15 Method 7.14, wherein the reaction solvent is toluene and the added non-polar solvent is a heptane (e.g., heptanes or n-heptane).

7.16 Method 7.14 or 7.15, wherein the precipitated solid (e.g., filter cake) is slurried with aqueous inorganic base (e.g., aqueous NaOH, KOH or NH$_4$OH) followed by filtration and washing with water.

7.17 Method 7.16, wherein the precipitated solid is slurried with aqueous ammonium hydroxide followed by filtration and washing with water.

7.18 Method 1F or 2F, or any of 7.1 et seq., wherein the compound of Formula 1F or 2F is obtained as a solid, e.g., as an amorphous or crystalline solid.

7.19 Method 1F or 2F, or any of 7.1 et seq., wherein the compound of Formula 1F or 2F is obtained in substantially pure form, e.g., greater than 90 wt % pure, or, e.g., greater than 95 wt % pure, up to 100 wt % pure.

7.20 Method 1F or 2F, or any of 7.1 et seq., wherein the compound of Formula 1F or 2F is obtained in free form (i.e., free base form), optionally as a crystalline solid.

7.21 Method 1F or 2F, or any of 7.1 et seq., wherein the compound of Formula 1F or 2F is obtained in a form having less than about 50 ppm of copper, or less than about 10 ppm of copper, or less than about 5 ppm of copper.

In some embodiments, any of Methods 1F, 2F, 1I, 2I, 1J, 2J, or 5.1-5.56 or 6.1-6.92, or 7.1-7.21, may further comprise the step of preparing a compound of Formula 1C or 2C:

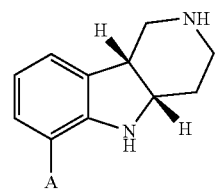

1C

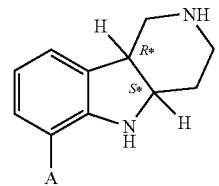

2C in free or salt form, comprising the sub-steps of:
a) reducing a compound of Formula 1A:

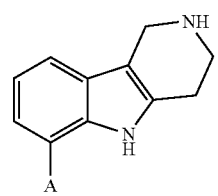

1A to a compound of Formula 1B:

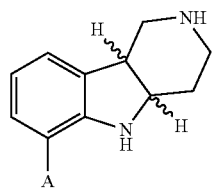

1B wherein substituent A of the compounds of Formulas 1A, 1B, 1C and/or 2C is selected from Br, Cl and I; and b) separating the stereoisomers (e.g., enantiomers) of compounds of Formula 1B by chiral acid resolution or chiral chromatography to yield the compound of Formula 1C or 2C; optionally wherein the compound of Formula 1C or 2C is at least 70%, preferably at least 80%, more preferably at least 90%, most preferably greater than 95%, and up to 100%, cis stereoisomer relative to all other stereoisomers; and/or wherein the compound of Formula 1C or 2C has an enantiomeric excess (e.e.) (e.g., of the 4aS, 9bR enantiomer, or of the 4aR, 9bS enantiomer) of at least 70%, preferably at least 80%, more preferably at least 90%, most preferably greater than 95% or greater than 97% or greater than 99% or greater than 99.9%, and up to 100%.

The reduction of Compounds of Formula 1A to Compounds of Formula 1B may be accomplished through the use of a reducing agent including, but not limited to: silanes in the presence of an acid (e.g., acetic, methanesulfonic acid or trifluoroacetic acid); metal (e.g., zinc) and mineral acid (e.g. hydrochloric acid); sodium and liquid ammonia; sodium in ethanol; or through the use of borane-amine complexes (e.g. borane-triethylamine in tetrahydrofuran); sodium triacetoxyborohydride; or sodium cyanoborohydride. The conversion of the Compound of Formula 1A to a Compound of Formula 1B may also be accomplished through catalytic hydrogenation, in which the Compound of Formula 1A is treated with hydrogen in the presence of a catalyst such as palladium oxide, palladium on carbon or platinum oxide (See Hudlicky, M., "Reductions in Organic Chemistry", Ellis Horwood, Ltd., Chichester, UK, 1984). The reduction of the Compound of Formula 2A to the Compound of Formula 2B may be accomplished through the use of similar agents as described for the reduction of Compounds of Formula 1A to 1B, for example silanes (e.g., triethylsilane) in the presence of an acid (e.g., acetic, methanesulfonic or trifluoroacetic acid); metal (e.g., zinc) and mineral acid (e.g. hydrochloric acid); sodium and liquid ammonia; sodium in ethanol; or through the use of borane-amine complexes (e.g. borane-triethylamine in tetrahydrofuran); sodium triacetoxyborohydride; or sodium cyanoborohydride. The conversion of the Compound of Formula 2A to the Compound of Formula 2B may also be accomplished through catalytic hydrogenation, in which the Compound of Formula 2A is treated with hydrogen in the presence of a catalyst such as palladium oxide, palladium on carbon or platinum oxide. In an especially preferred embodiment for the reduction of Compounds of Formula 1A or 2A, the reduction is accomplished through the use of triethylsilane in the presence of trifluoroacetic acid, or triethylsilane in the presence of methanesulfonic acid. In particular, it was unexpectedly found that substituting methanesulfonic acid for trifluoroacetic acid significantly improves yield, reaction time and cost efficiency. For example, using 4 volumes of methanesulfonic acid instead of 10 volumes of trifluoroacetic acid permits a significant reduction in need for the costly triethylsilane reagent (From 7 volumes to 1.3 volumes) and reduces reaction time from 45 hours to 2-5 hours, while increasing yield for the step.

In some embodiments, enantiomeric enrichment (or separation) of the isomers of the Compounds of Formula 1B to produce the Compounds of Formula 1C or 2C may be achieved by chiral salt resolution, in which chiral acids such as chiral sulfonic acids or mono- or di-carboxylic acids or derivatives thereof are used. Examples of such acids include, but are not limited to, (+/−)/(R/S) tartaric acid, (+/−)/(R/S) (mono- or di-acetyl)tartaric acid, (+/−)/(R/S) (mono- or di-benzoyl)tartaric acid, (+/−)/(R/S) (mono- or di-pivaloyl) tartaric acid, (+/−)/(R/S) mandelic acid, (+/−)/(R/S) acetoxyphenyl acetic acid, (+/−)/(R/S) methoxyphenyl acetic acid, (+/−)/(R/S) hydroxymandelic acid, (+/−)/(R/S) halomandelic acid (e.g. 4-fluoromandelic acid), (+/−)/(R/S) lactic acid, and (+/−)/(R/S) camphor sulfonic acid. Similarly, the enantiomeric separation of compounds of Formula 2B may be achieved by chiral salt resolution wherein chiral acids such as chiral sulfonic acids or mono- or di-carboxylic acids or derivatives thereof are used. Examples of such acids include, but are not limited to, (+/−)/(R/S) tartaric acid, (+/−)/(R/S) (mono- or di-acetyl)tartaric acid, (+/−)/(R/S) (mono- or di-benzoyl)tartaric acid, (+/−)/(R/S) (mono- or di-pivaloyl)tartaric acid, (+/−)/(R/S) mandelic acid, (+/−)/(R/S) acetoxyphenyl acetic acid, (+/−)/(R/S) methoxyphenyl acetic acid, (+/−)/(R/S) hydroxymandelic acid, (+/−)/(R/S) halomandelic acid (e.g. 4-fluoromandelic acid), (+/−)/(R/S) lactic acid, and (+/−)/(R/S) camphor sulfonic acid. Preferably, resolution of compounds of Formula 1B or 2B is accomplished by using mandelic acid. In an especially preferred embodiment, said acid is (S)-(+)-mandelic acid. Resolution may be optimized where undesired enantiomer is removed first. Therefore, in another preferred embodiment, resolution is accomplished by adding (R)-(−)-mandelic acid to remove the undesired enantiomer first, followed by the addition of (S)-(+)-mandelic acid to obtain the desired product. In some embodiments, only a single resolution is performed using only (S)-(+)-mandelic acid. Preferred solvents for the resolution include methanol, ethanol, methyl tert-butyl ether (MTBE), and combinations thereof.

In another embodiment, enantiomeric enrichment (or separation) of the stereoisomers of the Compounds of Formula 1B may be achieved by using chiral chromatography, for example using amylose tris(3,5-dimethylphenylcarbamate) column sold under the tradename "CHIRALPAK® AD®". The isomers of Formula 1B may be separated and eluted with a mobile phase such as ethanol at a flow rate of 100-450 mL/min. In yet another embodiment, the isomers of Formula 1B may be separated and eluted with mobile phase such as methanol or isopropyl alcohol. The fractions for the desired compounds, preferably, Compounds of Formula 1C or 2C, may be collected and isolated. In one embodiment, chiral chromatography comprises the use of CHIRALPAK® AD®, 20 µm, 5 cm ID×50 cm L column and 100% ethanol mobile phase at a flow rate of 150 mL/min. In another embodiment, chiral chromatography comprises the use of CHIRALPAK® AD®, 20 µm, 11 cm ID×25 cm L column and 100% ethanol mobile phase at a flow rate of 400 mL/min.

It is understood that upon the separation of the isomers of the Compounds of Formula 1B to yield the Compounds of Formula 1C or 2C, the diastereomeric or enantiomeric composition of the Compounds becomes fixed, or substantially fixed, as all further reactions in the sequence arriving at the Compound of Formula 1J or 2J does not substantially change the diastereomeric or enantiomeric composition of the Compounds. Thus, in all aspects and embodiments of the present disclosure, each of the intermediates according to Formulas 1D, 1E, 1F, 1H, and 1I, may each be substantially, essentially, or completely a single cis enantiomer, to the substantial or complete exclusion of the opposite cis isomer or any trans isomer. Likewise, in all aspects and embodiments of the present disclosure, each of the intermediates according to Formulas 2D, 2E, 2F, 2H, and 2I, may each be substantially, essentially, or completely a single cis enantiomer, specifically the 4aS, 9bR enantiomer, to the substantial or complete exclusion of the opposite cis isomer or any trans isomer. Thus, as used herein, each of the intermediates according to Formulas 1D, 2D, 1E, 2E, 1F, 2F, 1H, 2H, 1I and 2I, may be at least 70%, preferably at least 80%, more preferably at least 90%, most preferably greater than 95%, and up to 100%, cis stereoisomer relative to all other stereoisomers; and/or have an enantiomeric excess (e.e.) of at least 70%, preferably at least 80%, more preferably at least 90%, most preferably greater than 95%, or greater than 97%, or greater than 98.5%, or greater than 99%, or greater than 99.9%, and up to 100%.

In some embodiments, any of Methods 1F, 2F, 1I, 2I, 1J, 2J, or 5.1-5.56 or 6.1-6.92, or 7.1-7.21, may further comprise the step of preparing the compound of Formula 1A, in free or salt form, by reacting 2-bromophenylhydrazine with 4-piperidinone in an acidic solvent (a Fischer Indole reaction). In some embodiments the 2-bromophenylhydrazine and/or the 4-piperidinone is provided as an acid addition salt, for example, a hydrochloride, hydrobromide, acetate or trifluoroacetate salt. In some embodiments, the 4-piperidinone is present as a hydrate, e.g., a monohydrate. In some embodiments, the product is obtained as an acid addition salt, e.g., a hydrochloride, hydrobromide, trifluoroacetate, sulfate, or acetate salt. The reaction may be carried out in any suitable solvent, for example, an aqueous or alcoholic solvent (e.g., water, methanol, ethanol or isopropanol, or any mixture thereof) comprising a dissolved acid (e.g., HCl, HBr, $H_2SO_4$, acetic acid), or in a neat acidic solvent (e.g., acetic acid, trifluoroacetic acid). In some embodiments, the yield may be improved by using a solvent in which the product is poorly soluble. In some embodiments, the yield is improved by using neat acetic acid as the solvent.

In some embodiments, any of Methods 1F, 2F, 1I, 2I, 1 J, 2J, or 5.1-5.56 or 6.1-6.92, or 7.1-7.21 may further comprise the step of preparing a compound of Formula 1D or 2D:

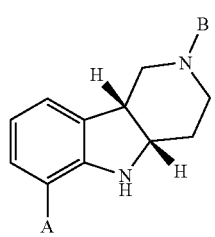

1D

-continued

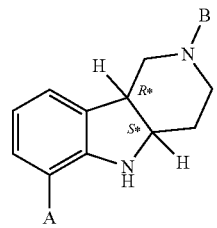

2D wherein:
(i) A is selected from Br, Cl and I; and
(ii) B is a protecting group, as defined herein;
in free or salt form, comprising the step of protecting the piperidine amine of the compound of Formula 1C or 2C with a protecting agent in the presence of a base;
wherein said protecting agent is a compound of the general formula:

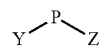

wherein:
(i) Y is halogen, imidazoyl, benzotriazole, N-(oxy)succinimide, alkoxy, —O— alkylaryl or —O-aryl;
(ii) Z is optionally substituted alkyl, aryl, alkylaryl or —OR wherein R is alkyl, aryl, arylalkyl or heteroarylalkyl;
(iii) P is —$CH_2$—, —C(O)—, —C(O)O— or $S(O)_2$.

Examples of suitable protecting agent for reaction with the compounds of Formula 1C or 2C include, but are not limited to, benzyloxycarbonyl chloride (Cbz-Cl), triphenylmethyl chloride, ethyl chloroformate, t-butoxycarbonyl anhydride ($Boc_2O$), benzyl N-succinimidyl carbonate, or benzoyl halide (e.g. benzoyl chloride or bromide), (benzyloxycarbonyl)-benzo triazole, benzyl halide (e.g. benzyl chloride or bromide), 1-arene sulfonyl chloride or toluene sulfonyl chloride. Another example of a protecting group of Compounds of Formula 1C or 2C is p-methoxybenzyl, which may be prepared using p-methoxybenzyl chloride, p-methoxybenzyl bromide or p-methoxybenzaldehyde. The protective agents disclosed herein are not intended to be exhaustive. For further examples of amine protecting agent, see one of the many general texts on the subject, for example, "Protective Groups in Organic Synthesis" by Theodora Green (publisher: John Wiley & Sons), the disclosure of which is hereby incorporated by reference. Upon addition of the protecting agent to the compounds of Formula 1C or 2C, the substituent B of the resulting compound 1D or 2D therefore has the general formula:

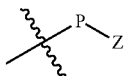

wherein:
(i) Z is optionally substituted alkyl, aryl, alkylaryl or —OR wherein R is alkyl, aryl, arylalkyl or heteroarylalkyl;
(ii) P is —$CH_2$—, —C(O)—, —C(O)O— or $S(O)_2$.

The protection step of this embodiment generally requires the addition of a base such as: butyl lithium or metal hydrides (e.g., potassium hydride); bicarbonates, carbonates, or hydroxides of alkali or alkaline earth metals (e.g., potassium or sodium carbonate, sodium bicarbonate, or sodium hydroxide), or organic amines (e.g., triethylamine). Preferably, the protecting agent of compounds of Formula 1D or 2D is ethyl chloroformate or BOC anhydride. In an especially preferred embodiment, said protecting agent is ethyl chloroformate and said base is triethylamine or sodium hydroxide.

In some embodiments, the conversion of the compound of Formula 1C or 2C to the compound of Formula 1D or 2D comprises treatment with ethyl chloroformate and sodium hydroxide in a mixture of water and THF.

In some embodiments, the procedure for protecting the piperidine nitrogen of the compound of Formula 1C or 2C will entail first neutralizing a salt of the compound of Formula 1C or 2C, for example a mandelic acid salt, with a suitable base, followed by isolation, separation, or purification of the free base of the compound of Formula 1C or 2C. The appropriate reagents for the protection of the piperidine nitrogen of the compound of Formula 1C or 2C are then added, along with suitable base to yield the compound of Formula 1D or 2D. The base used for neutralization may or may not be the base used for the protection reaction. In other embodiments, the salt of the compound of Formula 1C or 2C (e.g., the mandelate salt) is reacted with the appropriate protection reagents in the presence of excess base, in order to arrive at the compound of Formula 1D or 2D in a single step. Thus, the free base formation and acylation reactions are conducted simultaneously in these embodiments. Preferably the base is sodium hydroxide.

In some embodiments, any of Methods 1F, 2F, 1I, 2I, 1 J, 2J, or 5.1-5.52 or 6.1-6.92, or 7.1-7.21, may further comprise the step of preparing a compound of Formula 1E or 2E:

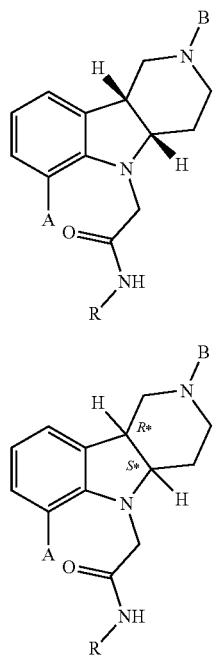

wherein:
(i) A is selected from Br, Cl and I;
(ii) R is selected from H and $C_{1-4}$alkyl (e.g. methyl); and
(iii) B is a protecting group, as defined herein;
in free or salt form, comprising the step of N-alkylating a compound of Formula 1D or 2D, as hereinbefore described, with (a) a nucleophilic alkyl halide of the general formula:

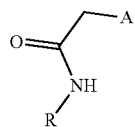

wherein:
(i) A=Cl, F, Br or I; and
(ii) R is H or $C_{1-4}$alkyl;
and (b) a base, and optionally (c) a catalyst (e.g., an iodide or bromide source).

In a further aspect, the present disclosure provides a method of making a compound of Formula 1D or 2D, as defined above, comprising the step of N-alkylating a compound of Formula 1D or 2D with (a) a nucleophilic alkyl halide, (b) a base, and (c) a catalyst, in a suitable solvent, as described herein below.

Examples of nucleophilic alkyl halides suitable for the alkylation of the compounds of Formula 1D and 2D include, but are not limited to, 2-chloroacetamide, 2-bromoacetamide, N—$C_{1-4}$ alkyl 2-chloroacetamides (e.g., N-methyl 2-chloroacetamide), and N—$C_{1-4}$alkyl 2-bromoacetamides (e.g., N-methyl 2-bromoacetamide). Examples of bases useful for said alkylation include, but are not limited to, organic bases such as amine bases (e.g., ammonia, triethylamine, N,N'-diisopropylethylamine or 4-(dimethylamino)pyridine (DMAP), 1,5-diazabicycl[4.3.0]-non-5-ene (DBN), 1,5-diazabicyclo[5.4.0]undec-5-ene (DBU)); or inorganic bases such as hydrides (e.g. sodium, lithium or potassium hydride), alkoxides (e.g. sodium, potassium or lithium t-butoxide and K(OAr), Na(OAr)), or carbonates, bicarbonates, phosphates or hydroxides of alkali or alkaline earth metals (e.g. sodium, magnesium, calcium, potassium, cesium or barium carbonate, bicarbonate, hydroxide or phosphate). Optionally, such N-alkylation reaction may be achieved in the presence of an iodide or bromide source, such as an alkali metal or ammonium iodide or bromide. For example, potassium iodide or sodium iodide, or potassium bromide or sodium bromide, a tetra-alkyl ammonium iodide (e.g., tetrabutylammonium iodide), or a tetra-alkyl ammonium bromide (e.g., tetrabutylammonium bromide). In particular embodiments, the alkylation may be carried out using 2-chloroacetamide or N-methyl 2-chloroacetamide in the presence of N,N'-diisopropylethylamine and potassium iodide in dimethylacetamide solvent. Suitable solvents also include acetonitrile, dioxane, dimethylformamide and dimethylacetamide.

In a preferred embodiment, the alkylation of the compound of the Formula 1D or 2D is carried out using 2-chloroacetamide, N,N-diisopropylethylamine, and tetrabutylammonium iodide or bromide, in a suitable solvent, such as dimethylacetamide, at a temperature of 90 to 110° C. The present inventors have unexpectedly found that on scale-up of the prior art methods for making the compound of Formula 1E or 2E, there was a concern for exothermic autocatalytic decomposition at temperatures near the prior reaction temperature (i.e., at about 120° C. or above). The inventors therefore carried out an expansive re-evaluation campaign to find an alternate set of reaction conditions. Factors which were evaluated included concentration, temperature, dosing of reagents, molar ratios, solvent choice (e.g., dimethylacetamide, N-methyl pyrrolidone, DMSO, acetone and acetonitrile), catalyst choice (e.g., alkali metal halides such as KI and KBr; ammonium salts such as tetrabutylammonium iodide or bromide; leaving group of the nucleophilic alkyl halide (e.g., Cl or Br), and base choice (e.g., amine bases such as DIPEA, hydride bases such as NaH, inorganic bases such as sodium or potassium carbonate). It was unexpectedly found that improved results are obtained using tetralkyl ammonium halide catalyst (e.g., tetrabutyl ammonium iodide or bromide), in an amount of about 0.5 to 1.5 equivalents, e.g., 0.75 to 1.25 equivalents, or 0.9 to 1.10 equivalents (e.g. about 1.0 equivalents), with a tertiary amine base (e.g., DIPEA at 1.5-1.9 equivalents, e.g., about 1.7 equivalents), and 2-chloroacetamide in dimethylacetamide solvent. Preferably, the temperature is from 90 to 110° C., such as 95 to 100° C. Because this method provides slightly lower yields than prior art methods, it was further unexpectedly found that advantage could be taken of the solubility difference between the compounds of Formula 1D/2D and 1E/2E in ethyl acetate. Therefore, in a preferred embodiment, the step of preparing the compound of Formula 1E or 2E, comprises the step of resuspending the crude product in ethyl acetate solvent, optionally as a mixture with n-hexane solvent, and isolating the product by crystallization at a temperature of 5 to 70° C.

In another aspect, the present disclosure provides an active pharmaceutical composition (active pharmaceutical ingredient) comprising the compound of Formula 1J or 2J, in substantially pure form. In further embodiments of this aspect, the present disclosure provides:

8.1 An active pharmaceutical composition (active pharmaceutical ingredient) comprising the compound of Formula 1J or 2J in pharmaceutically acceptable salt form, wherein the composition comprises at least 97% by weight of said compound (measured as the salt form), optionally in solid crystalline salt form (e.g., in tosylate salt form).

8.2 Composition 8.1, wherein the compound is the compound of Formula 1J, wherein R is H and Q is 3-(4-fluorophenoxy)propyl.

8.3 Composition 8.2, wherein said compound is in substantially enantiomerically pure form, e.g., at least 97% e.e., or in at least 98% e.e, or in at least 98.5% e.e., or in at least 99% e.e., up to 100% e.e.

8.4 Composition 8.2 or 8.3, wherein the composition comprises the compound is in at least 98%, at least 98.5% or at least 99.0% by weight (measured as the salt form).

8.5 Any of Compositions 8.2-8.4, wherein the compound is in free base form, optionally in solid crystalline free base form.

8.6 Any of Compositions 8.1 to 8.5, wherein the composition comprises not more than 2.0% by weight of each of any Compound of Formula 1A, 1B, 1C, 1D, 2D, 1E, 2E, 1F, 2F, 1I or 2I, for example, not more than 1.0% by weight of each, or not more than 0.50% by weight of each.

8.7 Any of Compositions 8.1 to 8.6, wherein the composition comprises not more than 2.0% by weight of a Compound of Formula 1I or 2I (e.g., wherein R is H), e.g., not more than 1.5% or not more than 1.0% or not more than 0.5% by weight.

8.8 Any of Compositions 8.1 to 8.7, wherein the composition comprises not more than 50 ppm of copper, e.g., not more than 40 ppm, or not more than 25 ppm, or not more than 10 ppm of copper, or not more than 5 ppm of copper.

8.9 Any of Compositions 8.1 to 8.8, wherein the composition comprises at least 0.001% by weight and less than 2% by weight of at least one compound selected from the compound of Formula 1K or 2K, or 1L or 2L.

8.10 Any of Compositions 8.1 to 8.8, wherein the composition comprises the compound of Formula 1J or 2J in admixture with at least 0.10% by weight and less than 2% by weight of at least one compound selected from the compound of Formula 1K or 2K, or 1L or 2L.

8.11 Any of Compositions 8.1 to 8.8, wherein the composition comprises the compound of Formula 1J or 2J in admixture with at least 1.0% by weight and less than 2.0% by weight of the compound of Formula 1K or 2K.

8.12 Any of Compositions 8.1 to 8.8, wherein the composition comprises the compound of Formula 1J or 2J in admixture with at least 1.0% by weight and less than 2.0% by weight of the compound of Formula 1L or 2L.

8.13 Any of Compositions 8.1 to 8.12, wherein the composition comprises the compound of Formula 1J or 2J in admixture with less than 1.0% by weight of 1-chloro-3-(4-fluorophenoxy)propane), e.g., less than 0.5%, or less than 0.25%, or less than 0.15% or less than 0.10%, or less than 0.08% by weight of 1-chloro-3-(4-fluorophenoxy)propane.

8.14 Any of Compositions 8.1 to 8.12, wherein the composition comprises the compound of Formula 1J or 2J in admixture with less than 5000 ppm of any organic solvent (e.g., acetone, acetonitrile or methanol), e.g., less than 4000 ppm, or less than 3000 ppm, or less than 1500 ppm, or less than 1000 ppm, or less than 500 ppm, or less than 410 ppm, of any such organic solvent.

8.15 Any of compositions 8.9 to 8.14, wherein in the compound of Formula 1K or 2K, or 1L or 2L, the group R is H and the group Q is —O—.

8.16 Any of Compositions 8.1 to 8.15, wherein the Compound of Formula 1J or 2J is a compound manufactured according to any of Methods 1J, 2J or 6.1-6.92.

In another aspect, the present disclosure provides a Pharmaceutical Composition comprising the active pharmaceutical composition (active pharmaceutical ingredient) according to any of compositions 8.1-8.16 in admixture with one or more pharmaceutically acceptable excipients, diluents, or solvents. In some embodiments, the Pharmaceutical Composition is selected from a tablet, capsule, caplet, powder, wafer, gel, or sterile injectable solution. In some embodiments, the Pharmaceutical Composition is an orally disintegrating tablet. In some embodiments, the Pharmaceutical Composition is a long-acting injectable composition, e.g., for intramuscular or subcutaneous administration. In some embodiments, the Pharmaceutical Composition comprises from 1 to 60 mg of the Compound of Formula 1J or 2J, measured by weight of the equivalent free base (e.g., from 20-60 mg, or 20-40 mg, or 40-60 mg, for an oral ingested dosage form; e.g., from 1-30 mg, or 5-20 mg, or 5-15 mg, or 1-10 mg, for an oral rapidly dissolving dosage form).

As used herein, "active pharmaceutical composition" refers to an active pharmaceutical ingredient (API) intended for incorporation into a pharmaceutical composition for administration to the body of a human or animal subject. As such, an API consists only of the active medicinal compound (e.g., the compound of Formula 1J or 2J) and any incidental impurities resulting from its synthesis. In contrast a "pharmaceutical composition" comprises an API in admixture with at least one excipient, diluent, or solvent. Suitable excipients, diluents and solvents are known in the art and include, but are not limited to, binders, disintegrants, polymers, sugars, fillers, sweeteners, adhesives, buffers, release-modulating agents, protective coatings (e.g., gastric coatings), colorants, flavors, and liquid carriers (including water, ethanol, glycerol, sorbitol, propylene glycol, and the like).

The compounds described herein and their pharmaceutically acceptable salts may be made using the methods as described and exemplified herein and by methods similar thereto and by methods known in the chemical art. In the description of the synthetic methods described herein, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Therefore, at times, any reaction may be required to run at an elevated temperature or for a longer or shorter period of time than described herein. It is understood by one skilled in the art of organic synthesis that functionality present on various portions of the molecule must be compatible with the reagents and reactions proposed. If not commercially available, starting materials for these processes may be made by procedures which are selected from the chemical art using techniques similar or analogous to the synthesis of known compounds. All references cited herein are hereby incorporated by reference in their entirety.

Unless the terms are specifically defined for an embodiment, the terms used herein are generally defined as follows.

The phrase "pharmaceutically acceptable salts" refers to derivatives of the disclosed compounds wherein the parent compound is modified by making acid or base addition salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric acid; and the salts prepared from organic acids such as toluenesulfonic acid.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media are preferred. Compounds of the present disclosure, have more than one basic nitrogen atom. For example, compounds of Formula 1J and 2J each have two basic nitrogen atoms (one N-aryl piperazine nitrogen, and one aliphatic piperidine nitrogen). It is understood that the piperidine nitrogen is more basic than the piperazine nitrogen. It is also understood that any one or both of these nitrogen atoms can form an acid addition salt with an acidic hydrogen of a monoprotic, diprotic or triprotic Bronsted acid, depending on the molar ratio of free base to acid provided in a reaction. As a result, when terms such as "acid addition salt" are used in this disclosure, such term refers to any such salts that are possible, as well as combinations thereof.

The term "alkyl" is intended to include both branched and straight-chain saturated aliphatic hydrocarbon groups having the specified number of carbon atoms; for example, "$C_1$-$C_4$ alkyl" denotes alkyl having 1 to 4 carbon atoms.

Examples of alkyl include, but are not limited to, methyl, ethyl, n-propyl, isopropyl, n-butyl, isobutyl, sec-butyl, and tert-butyl.

"Halo", "halogen" or "halide" as used herein refers to fluoro, chloro, bromo, and iodo. Therefore, "alkyl halide" refers to a halogen group attached to an alkyl group as defined above, such as methyl iodide or iodobutane.

"Alkali metal" refers lithium sodium and potassium. "Ammonium" refers to both the ammonium ion ($NH_4^+$) and tetraalkylammonium ions ($NR_4^+$), wherein R is a $C_{1-6}$ alkyl radical. For example, tetraalkylammonium includes tetramethylammonium, tetraethylammonium, tetrapropylammonium and tetrabutylammonium. Thus, the term "alkali metal or ammonium iodide or bromide" includes, but is not limited to, the iodide and bromide salts of sodium, potassium lithium, ammonium and tetraalkylammonium.

"Cycloalkyl" is intended to include monocyclic or polycyclic ring systems comprising at least one aliphatic ring. Therefore, "cycloalkyl" includes cyclopropyl, cyclobutyl, cyclopentyl, cyclopentenyl, cyclohexyl, cyclohexenyl and the like. Wherein cycloalkyl is a polycyclic system, such system may contain an aliphatic ring fused to an aromatic, non-aromatic, heteroaromatic or hetero nonaromatic rings. Examples of such include octahydro-1H-indene, 2,3-dihydro-1H-indene and 5,6,7,8-tetrahydroquinoline.

The term "heterocycloalkyl" herein refers to a monocyclic or polycyclic system comprising at least one aliphatic ring containing at least one heteroatom selected from a group consisting of O, N and S. Therefore, heterocycloalkyl may refer to piperidinyl, piperazinyl, 2-pyrrolidonyl, 1,2,3,4-tetrahydroquinolinyl, 2H,6H-1,5,2-dithiazinyl, 2H-pyrrolyl or 1,2,3,4-tetrahydro-1,8-naphthyridine.

As used herein, the term "aryl" is intended to mean a stable 5- to 7-membered monocyclic or polycyclic or 7- to 14-membered polycyclic ring system which comprises at least one aromatic ring (i.e., planar ring that contains 4n+2 Pi electrons, wherein n is an integer). Therefore, the term "aryl" includes phenyl, naphthyl and their derivatives. The term "aryl" is also intended to include polycyclic ring systems which contain at least one aromatic ring fused to one or more aromatic or non-aromatic or heteroaromatic rings (e.g., 2,3-dihydro-1H-indene).

As used herein, the term "heterocycle", "heterocyclic ring" or "heteroaryl" is intended to mean a stable 5- to 7-membered monocyclic or polycyclic or 7- to 14-membered polycyclic ring which comprises at least one aromatic ring containing at least one heteroatom independently selected from the group consisting of N, O and S. Therefore, a "heterocycle" or "heterocyclic ring" or "heteroaryl" may include a single heteroaromatic ring or a heteroaromatic ring fused to another heteroaromatic ring or to a non-heteroaromatic or non-aromatic ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of heterocycles or heteroaryl groups include, but are not limited to 1H-indazolyl, thiazolyl, furyl, pyridyl, quinolinyl, pyrollyl, indolyl and 5,6,7,8-tetrahydroquinolinyl.

The term "substituted," as used herein, means that any one or more hydrogens on the designated atom is replaced with a selection from the indicated group, provided that the designated atom's normal valency is not exceeded, and that the substitution results in a stable compound. Therefore, optionally substituted alkyl may refer to an alkyl group as defined above whereby one or more hydrogens are replaced with a selection from the indicated group including, but not limited to, halogen, hydroxy, amino, sulfhydryl, alkyl, alkenyl, alkynyl, haloalkyl (e.g. $CH_2C_1$, $CF_3$, $CH_3CH_2Br$, etc.), amido, aryl, arylalkyl, heteroaryl, heteroarylalkyl, cycloalkyl, heterocycloalkyl, alkoxy, carboxy, carbonyl, silyl, alkylamino, alkylamido, nitro, cyano, halo, —S(O)-alkyl, —S(O)$_2$-alkyl, R-cycloalkyl, R-heterocycloalkyl, R—C(O)—, R—C(O)—OR', R—O—, —N(R)(R') wherein R and R' are independently H, alkyl, aryl, heteroaryl, cycloalkyl, heterocycloalkyl, arylalkyl, heteroarylalkyl, heteroarylalkyl or heterocycloalkyl.

The term "resolution" is a term of art and refers to the separation of a racemic mixture into its enantiomers by any means, including reacting a chiral organic acid or base with the components of the racemic mixture to form diastereomeric salts and separating said salts by, for example, crystallization techniques. The term "chiral salt resolution" refers to the separation of a racemic mixture into its enantiomers through the use of a chiral acid.

The term "chromatography" is well known in the art and refers to a technique of separating the components of a mixture by interacting it with a stationary phase and eluting the components of the mixture with a mobile phase such as ethanol, methanol, acetonitrile, water or mixtures thereof. The term "chiral chromatography" refers to chromatography wherein the stationary phase is chiral.

The term "chiral acid" refers to any optically active acid capable of forming diastereomeric salts with compounds of Formula 1B or 2B. The terms "mono or di-carboxylic acid" or "sulfonic acid" herein refers to any compound that contains one or two carboxylic functional groups and a sulfonic acid group respectively. Examples of such acids include but are not limited to (+/−)/(R/S) tartaric acid, (+/−)/(R/S) (mono- or di-acetyl)tartaric acid, (+/−)/(R/S) (mono- or di-benzoyl)tartaric acid, (+/−)/(R/S) (mono- or di-pivaloyl)tartaric acid, (+/−)/(R/S) mandelic acid, (+/−)/(R/S) acetoxyphenyl acetic acid, (+/−)/(R/S) methoxyphenyl acetic acid, (+/−)/(R/S) hydroxymandelic acid, (+/−)/(R/S) halomandelic acid (e.g. 4-fluoromandelic acid), (+/−)/(R/S) lactic acid, and (+/−)/(R/S) camphor sulfonic acid.

The term "protecting agent" refers to any compound that reacts with the atom for which protection is desired so as to block or mask its functionality. It is typically used to temporarily modify a potentially reactive chemical functional group so as to protect it from undesired chemical transformation. A desirable protecting agent is one which is compatible with or stable to the reaction condition and is easily cleaved off at a later point when protection is no longer desired.

The terms "protecting group" and "protective group" refer to removable chemical groups that are used to protect or mask reactive functional moieties during synthetic transformations. The term "protecting agent" refers to a reagent that is used to attach protecting a group to the functional moiety to be protected. For example, the protecting agent ethyl chloroformate is used to attach the protecting group ethoxycarbonyl, and the protecting agent BOC-anhydride is used to attach the protecting group t-butoxycarbonyl. Protecting groups, as defined herein, include groups with the general formula —P—Z, wherein Z is optionally substituted alkyl, aryl, alkylaryl, alkoxycarbonyl, or —OR wherein R is alkyl, aryl, arylalkyl or heteroarylalkyl, and wherein P is —CH$_2$—, —C(O)—, —C(O)O—, or S(O)$_2$. Examples of protecting groups include benzyloxycarbonyl (Cbz), triphenylmethyl, alkyloxy and aryloxy carbonyl (e.g., methoxycarbonyl, ethoxycarbonyl, t-butoxycarbonyl, phenoxycarbonyl), benzyl N-succinimidyl carbonyl, benzoyl, substituted benzoyl, substituted benzyloxycarbonyl, benzyl, substituted benzyl, and alkyl and aryl sulfonyl (e.g., methanesulfonyl, benzenesulfonyl, toluenesulfonyl). Further suitable protecting agents and protecting groups can be found, for example, in "Protective Groups in Organic Synthesis" by Theodora Green (publisher: John Wiley & Sons, Fourth Edition, 2007), the disclosure of which is hereby incorporated by reference in its entirety.

The term "deprotection" or "deprotect" or "deprotecting" refers to the act of removing or cleaving off a protecting group. The deprotection conditions for the above protecting groups necessarily vary with the choice of protecting group and may involve acid (e.g., hydrochloric, sulfuric, phosphoric or trifluoroacetic acid or a Lewis acid such as boron tris(trifluoroacetate)) or base (alkali metal hydroxide, e.g., lithium, potassium or sodium hydroxide) catalysis or catalytic hydrogenation condition (e.g., hydrogen and palladium-on-carbon).

The term "catalyst" herein refers to any substance or agent capable of affecting, inducing, increasing, influencing or promoting the reactivity of a compound or reaction without itself being consumed. The phrase "transition metal catalyst" refers to any metal having valence electrons in the d-orbitals, e.g. metals selected from one of Groups 3-12 of the periodic table. The catalysts useful for the methods of this invention include atoms, ions, salts or complexes of transition metals from Groups 8-11 of the Periodic Table. "Group 3-12 of the Periodic Table" refers to the groups of the Periodic Table as numbered according to the IUPAC system. Therefore, transition metals from Group 8-11 which include iron, ruthenium, osmium, cobalt, rhodium, iridium, nickel, palladium, platinum, copper, silver and gold. Examples of such catalysts include, but are not limited to CuI, CuCl, CuBr, CuBr$_2$, Cu(II) acetate, Cu$_2$Cl$_2$, Cu$_2$O, CuSO$_4$, Cu$_2$SO$_4$, Cu, Pd/C, PdCl$_2$, Pd(OAc)$_2$, (CH$_3$CN)$_2$PdCl$_2$, Pd[P(C$_6$H$_5$)$_3$]$_4$, bis(dibenzylideneacetone) palladium [Pd(dba)$_2$], tris(dibenzylideneacetone)dipalladium [Pd$_2$(dba)$_3$], Ni(acetylacetonate)$_2$, NiCl$_2$[P(C$_6$H$_5$)]$_2$ and Ni(1,5-cyclooctadiene)$_2$. Catalysts are typically, but not necessarily used in sub-stoichiometric amount relative to the reactants. Preferably, 0.5-20 mol %, most preferably, 10 mol % of the transition metal catalyst relative to the reactants is used.

The term "base" herein refers to organic or inorganic bases such as amine bases (e.g., ammonia, triethylamine, N,N'-diisopropylethylamine or 4-(dimethylamino)pyridine (DMAP); 1,5-diazabicycl[4.3.0]-non-5-ene (DBN), 1,5-diazabicyclo[5.4.0]undec-5-ene (DBU)); hydrides (e.g. sodium, lithium or potassium hydride); alkoxides, (e.g. sodium, potassium or lithium t-butoxide and K(OAr), Na(OAr)); or carbonates, bicarbonates, phosphates or hydroxides of an alkali or alkaline earth metal (e.g. sodium, magnesium, calcium, potassium, cesium or barium carbonate, bicarbonate, hydroxide or phosphate).

The term "Bronsted base" is art-recognized term and refers to an uncharged or charged atom or molecule, e.g., an oxide, amine, alkoxide, or carbonate, which is a proton acceptor. Examples of Bronsted base include, but are not limited to K$_3$PO$_4$, K$_2$CO$_3$, Na$_2$CO$_3$, Tl$_2$CO$_3$, Cs$_2$CO$_3$, K(OtBu), Li(OtBu), Na(OtBu), K(OPh), and Na(OPh), or mixtures thereof.

The term "Lewis base" is recognized in the art and refers to a chemical moiety capable of donating a pair of electrons under certain reaction conditions. Examples of Lewis bases include, but are not limited to, uncharged compounds such as alcohols, thiols, olefins, and amines (e.g., ammonia, triethylamine), and charged moieties such as alkoxides, thiolates, carbanions, and a variety of other organic anions.

The term "acid" herein refers to Lewis or Bronsted acid. Lewis acid is a term of art and refers to a chemical moiety capable of accept a pair of electrons (e.g., boron trifluoride). Bronsted acid refers to any chemical moiety capable of donating a proton (e.g., acetic acid, hydrochloric acid, phosphoric acid as well as other organic acids known in the art).

The term "ligand" refers to any atom, molecule or ion capable of donating or sharing one or more electrons through a coordinate and/or covalent bond with another central atom, typically a metal. "Monodentate ligand" refers to ligands that have one binding site to the central atom (e.g., pyridine or ammonia). "Bidentate ligand" refers to ligands that have two binding sites (e.g., N,N'-dimethylethylenediamine, N,N,N',N'-tetramethylethylenediamine or 1,10-phenathroline). Examples of useful ligands for group 8-11 transition metals include, but are not limited to, 2-phenylphenol, 2,6-dimethylphenol, 2-isopropylphenol, 1-naphthol, 8-hydroxyquinoline, 8-aminoquinoline, DBU, DBN, DABCO, 2-(dimethylamino)ethanol, N,N-diethyl salicylamide, 2-(dimethylamino)glycine, N,N,N',N'-tetramethyl-1,2-diaminoethane, 4,7-diphenyl-1,10-phenanthroline, 4,7-dimethyl-1, 10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, (methylimino)diacetic acid, cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, N,N'-dimethyl-1,2-diaminoethane, N,N-dimethyl-2-hydroxybenzamide, N,N-diethyl-2-hydroxybenzamide, fluoro-N,N-diethyl-2-hydroxybenzamide, chloro-N,N'-diethyl-2-hydroxybenzamide, (2-hydroxyphenyl)(pyrrolidin-1-yl)methanone, biphenyl-2-ol, 2-pyridylphenol, 1,2-benezenediamine, ammonia, N,N-dimethylformamide, dimethylsulfoxide, 1-methyl-2-pyrrolidinone or mixtures thereof as well as the biphenyl and binaphthyl ligands hereinbefore described. In certain embodiments, the amount of ligand used may be a stoichiometric or an excess amount. In other embodiments, the ligand may be used as a solvent for the reaction. Therefore, reagents such as N,N-dimethylformamide, dimethylsulfoxide, 1-methyl-2-pyrrolidinone or other liquid amines may serve as a solvent as well as ligand for the reaction.

The term "N,N'-dimethylethylenediamine" is used interchangeably with "N,N'-dimethyl-1,2-diaminoethane".

The phrase "nucleophilic alkyl halide" refers to any compound having both an alkyl halide functional group (electrophilic) and a nucleophilic functional group. The term "nucleophilic" or "nucleophile" is well recognized in the art and refers to a chemical moiety having a reactive pair of electrons.

The term "reduction" or "reducing" refers to the conversion of a functional group in a molecule from a higher oxidation state to a lower oxidation state. The term "reducing agent" or "reductive agent" refers to any compound or complex that is known in the field for its effects in converting a functional group in a molecule from a higher oxidation state to a lower oxidation state. Examples of reduction include both the reduction of a carbon-carbon double bond to a carbon-carbon single bond, and reduction of a carbonyl group (C=O) to a methylene (CH$_2$). The reduction may be achieved via a direct electron, hydride or hydrogen-atom transfer. Typical reducing agents useful for Methods 1C and 2C include metal hydrides (e.g., lithium aluminum hydride, sodium borohydride, sodium cyanoborohydride) and hydrogen in the presence of a catalyst (e.g., Raney nickel, palladium on charcoal, nickel boride, platinum metal or its oxide, rhodium, ruthenium and zinc oxide, pentacyanocobaltate(II) Co(CN)$_5^{3-}$). Catalytic hydrogenation is typically carried out at room temperature and at atmospheric pressure, but higher temperature and/or higher pressure may be required for more resistant double bonds. Other reducing agents useful for converting double bonds to single bonds include silane and acid; sodium cyanoborohydride and acid; zinc and acid; sodium and liquid ammonia; sodium in ethanol; and borane-triethylamine.

The term "alkylation" refers to the introduction of an alkyl radical onto an organic compound by substitution or addition. Therefore, the term "N-alkylation" refers to the introduction of an alkyl radical onto the nitrogen atom of the organic compound.

Procedures for the production of compounds described herein and for the carrying out of some of the steps of the methods described herein are known to those skilled in the art, and can be found, for example, in U.S. Pat. Nos. 8,309,722; 8,779,139; 9,315,504; 9,751,883; 8,648,077; 9,199,995; and 9,586,960; the contents of each of which are hereby incorporated by reference in their entireties.

EXAMPLES

Example 1: 6-bromo-2,3,4,5-tetrahydro-1H-pyrido[4,3-b]indole hydrochloric acid salt

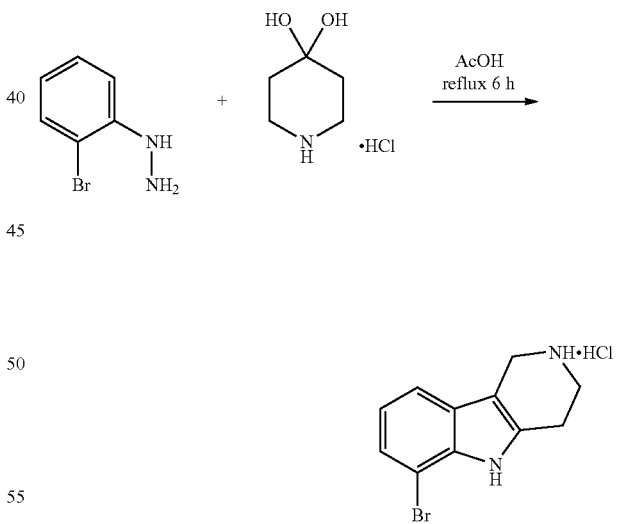

1-(2-bromophenyl)hydrazine hydrochloride and 4-piperidinone monohydrate hydrochloride are combined in about 1:1.1 molar ratio, in acetic acid, and the resulting slurry is heated to reflux until less than 1% of the hydrazine starting material remains by HPLC analysis (e.g., for 6 hours). The reaction mixture is then cooled to room temperature, filtered, and the cake is washed with acetone and dried to a solid which is used in the next step.

Example 2: [4aS, 9bR]-6-bromo-2,3,4,4a,5,9b-hexahydro-1H-pyrido[4,3-b]indole

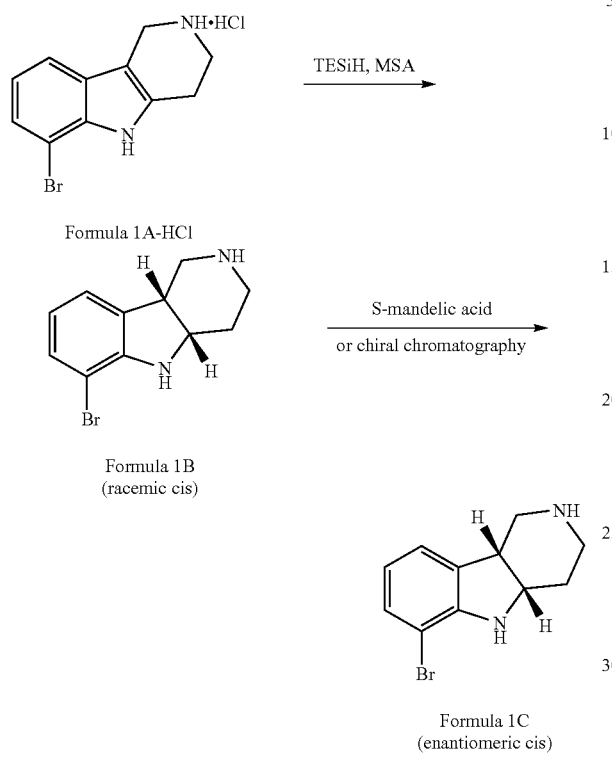

Formula 1A·HCl

Formula 1B
(racemic cis)

Formula 1C
(enantiomeric cis)

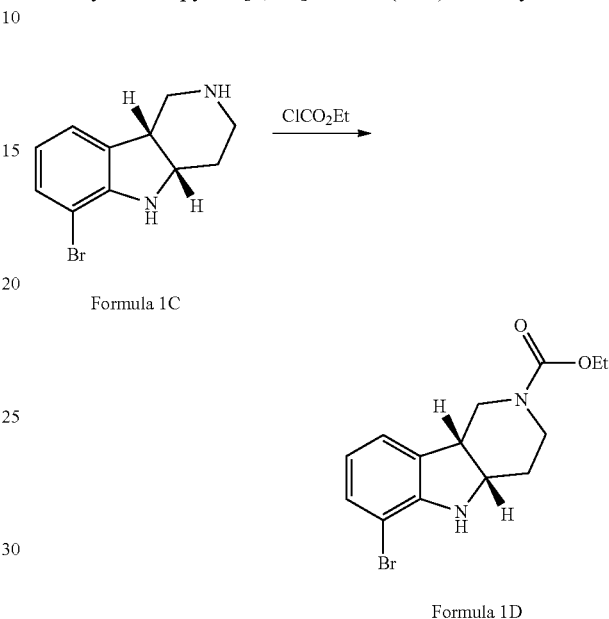

Formula 1C

Formula 1D

Reduction: To a 3 L 3-neck RBF with magnetic stirrer, N2 inlet and drying tube is charged methanesulfonic acid (400 mL). 6-bromo-2,3,4,4a,5,9b-tetrahydro-1H-pyrido[4,3-b]indole hydrochloric acid salt (100 g) is charged in portions. The reaction mixture is heated to 40° C. to 45° C., and then triethylsilane (TES) (55.5 mL, 1 eq.) is charged drop wise over 1 hour in order to control exotherm. The temperature is kept at 40° C. to 45° C. Once the addition is complete, the mixture is stirred at 40° C. to 45° C. for 1.5 h. Additional TES (13.9 mL, 0.25 eq.) may be added over approximately 10 minutes, after which, the mixture is stirred at 40° C. to 45° C. for 30 min. Additional TES (13.9 mL, 0.25 eq.) may be added over approximately 10 minutes, after which the mixture is stirred at room temperature overnight. Additional TES (5.5 mL, 0.1 eq.) may be charged and the mixture stirred at room temperature for 90 min. After cooling to <10° C., the reaction is quenched with water (600 mL) by adding water drop wise at a rate to maintain <40° C. (strong exotherm observed). Dichloromethane (1000 mL) is added and the mixture is adjusted to about pH=12 with 50% w/v aqueous NaOH. The mixture is filtered through a layer of Celite. The layers are separated and the aqueous layer is extracted with dichloromethane (100 mL). The combined organic layer is washed with water (100 mL), dried over magnesium sulfate (120 g), filtered and concentrated under vacuum. The residue is treated with heptanes. After filtration, the obtained solid is dried under vacuum at 30° C. to give 73.1 g of product (yield: 83%, HPLC purity: 97.1%).

Separation: [4aS, 9bR]-6-bromo-2,3,4,4a,5,9b-hexahydro-1H-pyrido[4,3-b]indole may be separated by dissolving the racemic cis 6-bromo-2,3,4,4a,5,9b-hexahydro-1H-pyrido[4,3-b]indole (9.61 g, 38.0 mmol) in methanol (190 mL) at 50° C. and adding (S)-(+)-Mandelic acid (5.78 g, 38.0 mmol) in portions. The resulting clear solution is stirred at 50° C. for several minutes and ether (95 mL) is added dropwise. The resulting solution is cooled to room temperature. The white precipitate (S-Mandelate salt, 4.1 g) is filtered off. HPLC analysis shows >99% e.e.

Example 3: (4aS,9bR)-ethyl 6-bromo-3,4,4a,5-tetrahydro-1H-pyrido[4,3-b]indole-2(9bH)-carboxylate (4aS,9bR)-ethyl 6-bromo-3,4,4a,5-tetrahydro-1H-pyrido[4,3-b]indole-2(9bH)-carboxylate may be prepared by first obtaining [4aS, 9bR]-6-bromo-2,3,4,4a,5,9b-hexahydro-1H-pyrido[4,3-b]indole (36.0 g, 0.142 mol)) as a free base by using 50% aqueous sodium hydroxide solution and extracting the product into MTBE. The conversion to (4aS, 9bR)-ethyl 6-bromo-3,4,4a,5-tetrahydro-1H-pyrido[4,3-b]indole-2(9bH)-carboxylate may then be done by cooling a suspension of [4aS, 9bR]-6-bromo-2,3,4,4a,5,9b-hexahydro-1H-pyrido[4,3-b]indole (36.0 g, 0.142 mol)) in THF (300 ml) and triethylamine (24 ml) in an ice-water bath. Ethyl chloroformate is added dropwise (13.5 ml, 0.142 mol) via a syringe pump over 1 hour. The ice-water bath is removed and the reaction mixture is stirred at room temperature for another hour. The reaction mixture is passed through a pad of Celite and the solvent is evaporated to give (4aS,9bR)-ethyl 6-bromo-3,4,4a,5-tetrahydro-1H-pyrido[4,3-b]indole-2(9bH)-carboxylate). $^1$H NMR (CDCl$_3$, 300 MHz): 1.20-1.35 (m, 3H), 1.73-1.85 (m, 1H), 1.85-1.99 (m, 1H), 3.22-3.52 (m, 3H), 3.52-3.66 (m, 1H), 3.66-3.95 (Br, 1H), 3.95-4.21 (m, 4H), 6.60 (t, J=7.7 Hz, 1H), 7.04 (d, J=7.2 Hz, 1H), 7.20 (d, J=8.1 Hz, 1H).

Alternative to the use of [4aS, 9bR]-6-bromo-2,3,4,4a,5,9b-hexahydro-1H-pyrido[4,3-b]indole (Compound of Formula 1C) free base, the reaction may also be carried out by starting with the (S)-mandelate salt of [4aS, 9bR]-6-bromo-2,3,4,4a,5,9b-hexahydro-1H-pyrido[4,3-b]indole. A 100 mL round-bottomed flask is equipped with a magnetic stirring bar, a pressure-equalizing addition funnel, and a N2 inlet on top of the addition funnel. The flask is charged with the S-mandelate starting material (5 g, 12.35 mmol), Na$_2$CO$_3$ (2.88 g, 27.17 mmol), and 25 mL of THF. To the yellow reaction mixture at 25° C. (heating block temperature) is added a solution of ethyl chloroformate (1.64 g, 15.11 mmol) in 5 mL of THF dropwise over ca 70 minutes. The batch is stirred at 25° C. for another 10 min, and then is checked by HPLC. Less than 2% of the starting material is observed by HPLC, and the desired product is registered at ca. 98%. To the batch is added 12.5 mL of EtOH, and the batch is concentrated under reduced pressure to remove about 30 mL of solvent (mostly THF). To the batch is then added 37.5 mL of $H_2O$, and the resultant mixture shows pH>9 by pH paper. The yellow mixture is then stirred at room temperature for about 1 h, and then is filtered. The solid is rinsed with 25 mL of $H_2O$. After drying in a vacuum oven at 58° C. for about 16 h, 3.9442 g of a yellow solid is obtained (98% yield). $^1$H NMR of the solid conformed and showed no (s)-mandelic acid. HPLC analysis of the product shows the desired product at >99% purity. LC-MS showed a peak with M/e=326 (M+1).

Example 4: [4aS,9bR]-ethyl 5-(2-amino-2-oxo-ethyl)-6-bromo-3,4,4a,5-tetrahydro-1H-pyrido[4,3-b]indole-2(9bH)-carboxylate Additional experiments reveal that on larger scales, the product may oil out, creating difficulties in handling and purification. It is unexpectedly found that controlling the rate of cooling and rate of water addition has a significant effect on this outcome. Therefore, in an improved method, the product is obtained from the dimethylacetamide reaction mixture by precipitative crystallization using water as antisolvent, optionally induced by seeding. For example, the reaction may be cooled to about 50-70° C. followed by addition of a portion of water, followed later by addition of more water. The mixture is stirred or agitated while cooling gradually to a final temperature of about 0-15° C. (e.g., 5° C.) followed by filtration and washing with water. During the cooling process, seeding is initiated to cause precipitation of the product.

Example 4b: 4aS,9bR]-ethyl 5-(2-amino-2-oxo-ethyl)-6-bromo-3,4,4a,5-tetrahydro-1H-pyrido[4,3-b]indole-2(9bH)-carboxylate

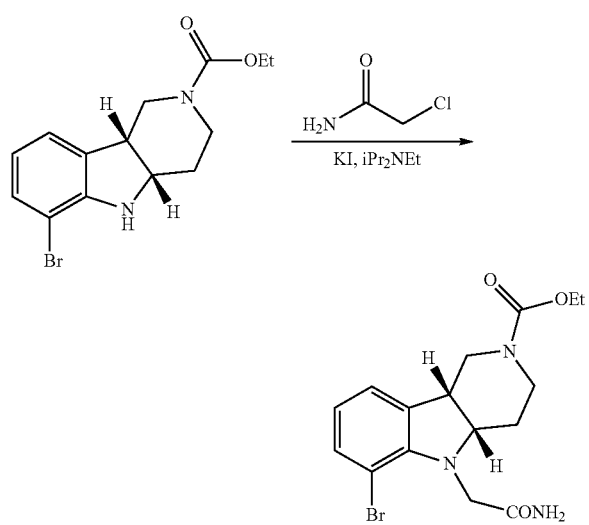

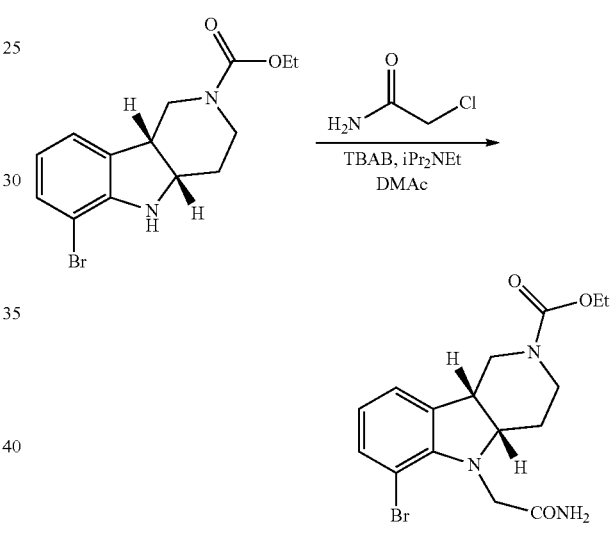

(4aS,9bR)-ethyl 5-(2-amino-2-oxoethyl)-6-bromo-3,4,4a,5-tetrahydro-1H-pyrido[4,3-b]indole-2(9bH)-carboxylate may be prepared by heating to a reflux a suspension of (4aS,9bR)-ethyl 6-bromo-3,4,4a,5-tetrahydro-1H-pyrido[4,3-b]indole-2(9bH)-carboxylate (5.648 g, 17.4 mmol), 2-chloroacetamide (7.32 g, 78.2 mmol), potassium iodide (19.2 g, 77.7 mol) and diisopropylethylamine (19 mL, 115 mmol) in acetonitrile (80 mL) for 27 hours. The solvent is removed in a vacuo and water (200 mL) is added to the residue and stirred for 1 hour. The resulting white solid is filtered off, washed with ethanol and dried.

In further experiments, it is found that yield and reaction time are improved by using substantially the same conditions with dimethyl acetamide solvent instead (e.g. at a temperature of 80 to 110° C., e.g., at 110° C.). In comparative experiments, it is found that higher yields are obtained using dimethyl acetamide compared to either acetonitrile or dioxane as solvent. Further experiments are also conducted using 2-bromoacetamide in dimethyl acetamide, acetonitrile, or dioxane solvent, optionally further comprising potassium iodide or tetrabutyl ammonium bromide.

(4aS,9bR)-ethyl 6-bromo-3,4,4a,5-tetrahydro-1H-pyrido[4,3-b]indole-2(9bH)-carboxylate (175 g, 538 mmol), 2-chloroacetamide (75.48 g, 807 mmol), tetrabutylammonium bromide (173.5 g, 538 mmol) and diisopropylethylamine (151 mL, 917 mmol) are suspended in dimethylacetamide (158 mL) at 107-110° C. for 24-27 hours. HPLC shows more than 85% completion. The reaction mixture is cooled to 50-55° C., and water is slowly added (350-400 mL) added, the mixture is stirred for 2 hours at about 50° C., and then the mixture is seeded with product (about 50 mg). Additional water (450-500 mL) is added over a 1 to 3 hour period, followed by a second seeding, and then the mixture is slowly cooled to 5° C. The suspension is filtered, and the filter cake is washed with water, dried under vacuum to yield 187 g of crude product (86% purity by HPLC). The crude product is resuspended in ethyl acetate at 70° C. and agitated for 2 hours. The suspension is cooled to 50° C. and n-heptane is added slowly to induce precipitation. After stirring for 2 hours at 50° C., the mixture is slowly cooled to 5° C., followed by filtration and washing with ethyl acetate/hexane (1:1). After drying, 149 g of pure product is obtained (98% purity by HPLC).

Example 5: (6bR,10aS)-ethyl 2,3,6b,9,10,10a-hexahydro-2-oxo-1H-pyrido[3',4':4,5]-pyrrolo[1,2,3-de]quinoxaline-8-carboxylate

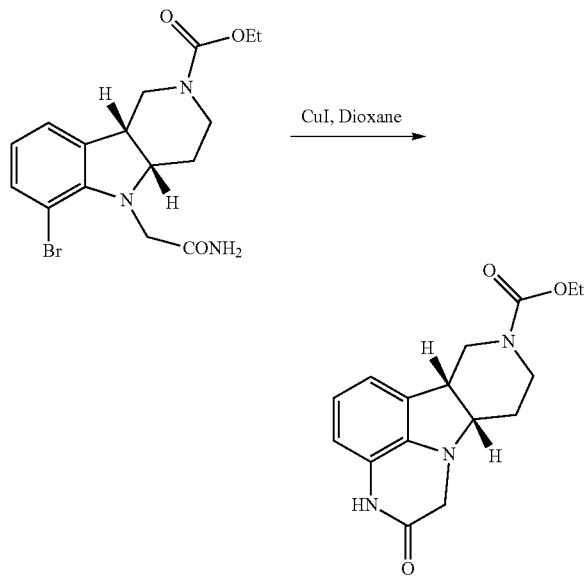

A suspension of [4aS,9bR]-ethyl 5-(2-amino-2-oxoethyl)-6-bromo-3,4,4a,5-tetrahydro-1H-pyrido[4,3-b]indole-2(9bH)-carboxylate (254 mg, 1.34 mmol), cuprous iodide (254 mg, 1.34 mol), potassium carbonate (3.96 g, 28.7 mmol) and N,N'-dimethyl ethylenediamine (0.31 mL, 2.87 mmol) in dioxane (20 mL) is heated at reflux for 4.5 hours. Another portion of cuprous iodide (250 mg, 1.32 mmol) and N,N'-dimethyl ethylenediamine (0.33 mL, 3.05 mmol) is added. The resulting mixture is heated to a reflux for another 3 hours and then at 73° C. for about 66 hours. The reaction mixture is concentrated and passed through a short alumina column using 100:3:3 dichloromethane: triethylamine: methanol. The resulting solvent from the column is evaporated to a solid and redissolved in dichloromethane. The dichloromethane solution is washed with brine, dried with sodium sulfate and concentrated to a solid (3.7 g, 95%, 83% pure by HPLC).

On scaling of this laboratory procedure to manufacturing batch scale (~1 kg scale), it is found that yield drops to 26% mainly due to losses during filtration. Even after reslurring the filter cake with methanol to recover additional product, net yield only approaches 86% with HPLC purity of about 70-75%. Without being bound by theory, it is believed that the losses are due to material lost during transfer between piping lines, reactors and other vessels.

Further experiments are conducted to optimize the reaction and purification conditions. Initial experiments using N,N,N',N'-tetramethylethylenediamine as the ligand (0.25 equiv.), with potassium iodide (1.9 equiv.), copper iodide (0.2 equiv.), and dioxane solvent result in reaction times of at least 48 hours to obtain acceptable yield. Furthermore, it is unexpectedly found that the product is sensitive to oxygen, and during extractive work-up and concentration of reaction solvent prior to chromatography, decomposition can occur. The reaction is also found to be sensitive to water content of the reaction solvent (dioxane being miscible with water, it permits significantly higher concentrations of water to be present compared to other solvents). It is found that using DBU as the ligand, toluene as the solvent, and azeotropic distillation prior to the reaction results in significantly improved yield and conversion. Yield is further improved by using hydrocarbon solvent to precipitate the free base product, rather than submitting the reaction mixture to extraction and/or evaporation.

[4aS,9bR]-ethyl 5-(2-amino-2-oxoethyl)-6-bromo-3,4,4a,5-tetrahydro-1H-pyrido[4,3-b]indole-2(9bH)-carboxylate (1400 g, 1.00 equiv.) and potassium carbonate (2.2 equiv.) are suspended in toluene solvent (4 mL/g of reactant) and the mixture is heated with a Dean-Stark trap at 110° C. for about 2 hours. Azeotropic distillation is continued until no further water is collected. After cooling to 70° C., copper iodide (0.2 equiv.) and DBU (0.25 equiv.) are added. After stirring for 7 hours at 120° C., it is found that the reaction is substantially complete (<3% starting material remaining by HPLC). The reaction mixture is cooled to room temperature and diluted with 10 volumes of degassed n-heptane with stirring. After stirring for 2 hours, a heavy suspension is obtained. The mixture is filtered and the collected solids are slurried with 7% aqueous ammonium hydroxide for one hour. The slurry is filtered and the solid is washed twice with water. The slurry/wash procedure is repeated twice again using 12.5% aqueous ammonium hydroxide (1 hour slurry each). The solid is dried to obtain the title product in 95% yield (95% HPLC purity).

Example 6: (6bR,10aS)-2,3,6b,7,8,9,10,10a-octahydro-1H-pyrido-[3',4':4,5]-pyrrolo[1,2,3-de]quinoxaline

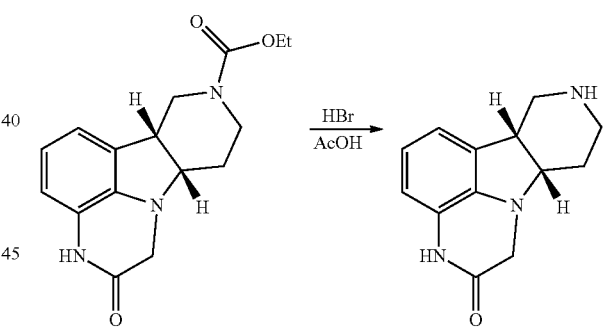

(6bR,10aS)-2-oxo-2,3,6b,9,10,10a-hexahydro-1H,7H-pyrido[3',4':4,5]-pyrrolo[1,2,3-de]quinoxaline-8-carboxylic acid ethyl ester (6.4 g, 21.2 mmol) is suspended in HBr/acetic acid solution (64 mL, 33% w/w) at room temperature. The mixture is heated at 50° C. for 16 hours. After cooling and treatment with ethyl acetate (300 mL), the mixture is filtered. The filter cake is washed with ethyl acetate (300 mL), and then dried under vacuum. The obtained HBr salt is then suspended in methanol (200 mL), and cooled with dry ice in isopropanol. Under vigorous stirring, ammonia solution (10 mL, 7N in methanol) is added slowly to the suspension to adjust the pH of the mixture to 10. The obtained mixture is dried under vacuum without further purification to give crude (6bR, 10aS)-2-oxo-2,3,6b,9,10,10a-hexahydro-1H,7H-pyrido[3',4':4,5]pyrrolo[1,2,3-de]quinoxaline (8.0 g), which is used directly in the next step. MS (ESI) m/z 230.2 [M+H]+.

Example 7: (6bR,10aS)-8-(3-(4-fluorophenoxy)pro-pyl)-6b,7,8,9,10,10a-hexahydro-1H-pyrido[3',4':4,5]pyrrolo[1,2,3-de]quinoxalin-2(3H)-one

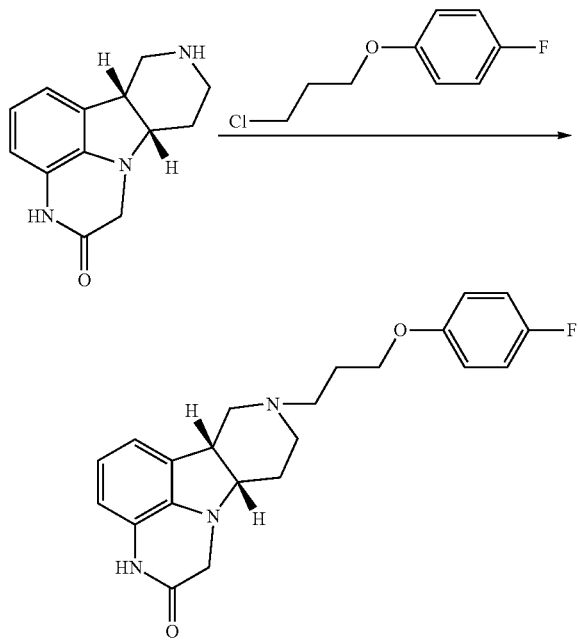

A mixture of (6bR,10aS)-6b,7,8,9,10,10a-hexahydro-1H-pyrido[3',4':4,5]pyrrolo[1,2,3-de]quinoxalin-2(3H)-one (100 mg, 0.436 mmol), 1-(3-chloroproxy)-4-fluorobenzene (100 μL, 0.65 mmol) and KI (144 mg, 0.87 mmol) in DMF (2 mL) is degassed with argon for 3 minutes and DIPEA (150 μL, 0.87 mmol) is added. The resulting mixture is heated to 78° C. and stirred at this temperature for 2 h. The mixture is cooled to room temperature and then filtered. The filter cake is purified by silica gel column chromatography using a gradient of 0-100% ethyl acetate in a mixture of methanol/7N $NH_3$ in methanol (1:0.1 v/v) as an eluent to produce partially purified product, which is further purified with a semi-preparative HPLC system using a gradient of 0-60% acetonitrile in water containing 0.1% formic acid over 16 min to obtain the title product as a solid (50 mg, yield 30%). MS (ESI) m/z 406.2 [M+1]$^+$. $^1$H NMR (500 MHz, DMSO-$d_6$) δ 10.3 (s, 1H), 7.2-7.1 (m, 2H), 7.0-6.9 (m, 2H), 6.8 (dd, J=1.03, 7.25 Hz, 1H), 6.6 (t, J=7.55 Hz, 1H), 6.6 (dd, J=1.07, 7.79 Hz, 1H), 4.0 (t, J=6.35 Hz, 2H), 3.8 (d, J=14.74 Hz, 1H), 3.3-3.2 (m, 3H), 2.9 (dd, J=6.35, 11.13 Hz, 1H), 2.7-2.6 (m, 1H), 2.5-2.3 (m, 2H), 2.1 (t, J=11.66 Hz, 1H), 2.0 (d, J=14.50 Hz, 1H), 1.9-1.8 (m, 3H), 1.7 (t, J=11.04 Hz, 1H).

In additional experiments, it is found that yield and purity are improved by conducting the reaction in DMSO solvent at 70-75° C. for 3-5 hours (97% conversion, 100 g-1 kg scale)). The product may be isolated by quenching with an ethyl acetate-water mixture, followed by solvent exchange with n-heptane after phase separation. The crude product may be isolated by crystallization from n-heptane, followed by filtration, washing and drying under vacuum. The crude product may be further purified by slurrying and filtering from acetonitrile. The obtained product conforms to expected 41-NMR, and HPLC-MS analysis. The following purity profile is obtained (organic impurities are determined by HPLC, except that solvent impurities are determined by HS-GC):

| Analyte | Amount (HPLC % area) |
|---|---|
| RRT 0.10 peak | 0.11% |
| RRT 0.11 peak | 0.51% |
| (6bR,10aS)-6b,7,8,9,10,10a-hexahydro-1H-pyrido[3',4':4,5]pyrrolo[1,2,3-de]quinoxalin-2(3H)-one | 0.18% |
| RRT 0.40 peak | 0.09% |
| RRT 0.94 peak | 0.09% |
| RRT 1.09 peak | 0.06% |
| (6bR, 10aS)-2-oxo-2,3,6b,9,10,10a-hexahydro-1H,7H-pyrido [3',4':4,5]pyrrolo[1,2,3-de]quinoxaline-8-carboxylic acid ethyl ester | 0.78% |
| RRT 1.23 peak | 0.10% |
| RRT 1.40 peak | 1.70% |
| Net HPLC Purity | 95.7% |
| n-hepane | 3716 ppm |
| DMSO | <500 ppm |
| Ethyl acetate | 13611 ppm |
| Toluene | 1463 ppm |

Example 8: Purification of (6bR,10aS)-8-(3-(4-fluorophenoxy)propyl)-6b,7,8,9,10,10a-hexahydro-1H-pyrido[3',4':4,5]pyrrolo[1,2,3-de]quinoxalin-2(3H)-one It was unexpectedly found during scale-up experiments that re-slurrying crude (6bR,10aS)-8-(3-(4-fluorophenoxy)propyl)-6b,7,8,9,10,10a-hexahydro-1H-pyrido[3',4':4,5]pyrrolo[1,2,3-de]quinoxalin-2(3H)-one in either acetonitrile or acetone resulted in overall acceptable HPLC purity for the purified product (93-97%), but having an excessive of amount of certain particular impurities, for example, of 1-(3-chloroproxy)-4-fluorobenzene, which is present in an amount of 0.10 to 0.30% w/w. This impurity should be limited to no more than 0.08% w/w in the final product.

A crystallization study is therefore performed to determine optimum conditions for further purification of the free base product. Initially screened solvents include methanol, ethanol, isopropanol, acetonitrile, acetone, methyl ethyl ketone, 2-methyltetrahydrofuran, ethyl acetate and isopropyl acetate. Based on initial screening results, further studies are limited to methanol, acetone and acetonitrile.

Initial results are shown in the table below:

| Analyte | Amount (HPLC % area) | | | |
|---|---|---|---|---|
| Recrystallization solvent: | Crude | Acetone | Acetonitrile | Methanol |
| RRT 0.11 peak | 0.41% | 0.09% | 0.14% | 0.04% |
| (6bR,10aS)-6b,7,8,9,10,10a-hexahydro-1H-pyrido[3',4':4,5]pyrrolo[1,2,3-de]quinoxalin-2(3H)-one | 0.24% | 0.05% | 0.07% | 0.02% |
| RRT 0.94 peak | 0.24% | 0.11% | 0.18% | 0.12% |
| (6bR, 10aS)-2-oxo-2,3,6b,9,10,10a-hexahydro-1H,7H-pyrido[3',4':4,5]pyrrolo[1,2,3-de]quinoxaline-8-carboxylic acid ethyl ester | 0.78% | 0.46% | 0.39% | 0.35% |
| RRT 1.40 peak | 1.35% | 0.13% | 0.12% | 0.05% |
| Net HPLC Purity | 95.5% | 98.8% | 98.6% | 99.1% |
| Net yield | | 70% | 82% | 77% |

When the above noted recrystallized products are each dried at 50° C. and 100 mbar vacuum, however, levels of residual solvent exceed ICH limits, as shown in the table below (24 hours drying for acetonitrile, 60 hours drying for methanol and acetone):

| Recrystallization solvent: | ICH Limit | Residual Solvent Level (ppm) | | |
|---|---|---|---|---|
| | | Acetonitrile | Methanol | Acetone |
| Acetonitrile | 410 ppm | 15900 | | |
| Methanol | 3000 ppm | | 5792 | |
| Acetone | 5000 ppm | | | 8249 |

This data shows that the product unexpectedly tends to entrap solvents in such a way that makes it very difficult to remove, even after prolonged periods of drying under vacuum. In combination with further studies, it is found that (6bR,10aS)-8-(3-(4-fluorophenoxy)propyl)-6b,7,8,9,10, 10a-hexahydro-1H-pyrido[3',4':4,5]pyrrolo[1,2,3-de]quinoxalin-2(3H)-one free base tends to entrap solvents in its crystal structure at about a 10 mol % amount.

Further studies show that the rate of cooling during crystallization has an impact on residual solvent levels. It is found that faster cooling (e.g., 20° C./hr versus 10° C./hr) helps to produce smaller-sized crystals which entrap less solvent. In contrast, drying the crystals at higher temperatures or lower pressure (higher vacuum) does not significantly influence residual solvent levels.

Further studies are performed to evaluate the role of antisolvents (e.g., n-heptane or MTBE) in the crystallization process. Without being bound by theory, it is suspected that by using a mixture of solvents, each solvent can be reduced to below ICH levels. However, each set of binary solvent mixtures must be analyzed to also ensure that recrystallization from the solvent mixture maintains sufficient overall HPLC purity and satisfactory impurity profile.

Various combinations of recrystallization solvent mixture are studied, including acetone-ethyl acetate and acetone-methanol, at various solvent ratios. It is found that acetone-methanol recrystallization at a 2:1 or 3:1 ratio provides satisfactory results, as shown in the table below:

| | Recrystallization Solvent Mixture | | | |
|---|---|---|---|---|
| | Acetone-EtOAc | | Acetone-Methanol | |
| Analyte | 3:1 | 2:1 | 2:1 | 3:1 |
| HPLC Purity (% area) | 97.4% | 97.0% | 99.2% | 99.2% |
| Acetone residual (ppm) | 4929 | 4743 | 2583 | 2570 |
| Ethyl Acetate residual (ppm) | 1931 | 3411 | <250 | <250 |
| Methanol residual (ppm) | | | 2470 | 1436 |
| Net yield | 66% | 69% | 65% | 68% |
| Individual Impurities (HPLC % area) | | | | |
| RRT 0.11 peak | 0.17% | 0.33% | 0.27% | 0.35% |
| (6bR,10aS)-6b,7,8,9,10,10a-hexahydro-1H-pyrido[3',4':4,5]pyrrolo[1,2,3-de]quinoxalin-2(3H)-one | 0.11% | 0.08% | 0.06% | 0.04% |
| RRT 0.94 peak | 0.08% | 0.10% | 0.07% | 0.09% |
| (6bR, 10aS)-2-oxo-2,3,6b,9,10,10a-hexahydro-1H,7H-pyrido[3',4':4,5]pyrrolo[1,2,3-de]quinoxaline-8-carboxylic acid ethyl ester | 0.47% | 0.48% | 0.33% | 0.27% |
| RRT 1.40 peak | 1.20% | 1.38% | <0.05% | <0.05% |
| 1-(3-chloroproxy)-4-fluorobenzene (w/w) | 0 | 0 | 0 | 0 |

All drying conditions for the crystals prepared above is 16 hours, 40° C. at 100 mbar.

Example 9: Purification of (6bR,10aS)-8-(3-(4-fluorophenoxy)propyl)-6b,7,8,9,10,10a-hexahydro-1H-pyrido[3',4':4,5]pyrrolo[1,2,3-de]quinoxalin-2(3H)-one tosylate (6bR,10aS)-8-(3-(4-fluorophenoxy)propyl)-6b,7,8,9,10, 10a-hexahydro-1H-pyrido[3',4':4,5]pyrrolo[1,2,3-de]quinoxalin-2(3H)-one in free base form (1.88 g) is added to a 20 mL vial. 11 mL of methyl ethyl ketone is added, and the reaction mixture is heated to 50° C., forming a brown suspension. Solid toluenesulfonic acid (1.5 eq,) is added and the mixture soon becomes a homogenous brown solution. While stirring at 50° C., crystallization of a product slowly begins. After stirring for about 1 hours, the heat is removed and the reaction mixture is allowed to cool to room temperature with stirring (stirring overnight). A brown suspension is obtained. The mixture is filtered and washed with methyl ethyl ketone under vacuum to yield 1.7 grams of an off-white to brownish powder. The powder slowly turns purple at room temperature. XRPD analysis shows sharp peaks, characteristic of a good crystalline material, but with some amorphous background present. 1H-NMR is consistent with a monotosylate salt (1:1 molar ratio of tosyl protons to free base protons). Further studies show that the salt is hygroscopic.

What is claimed is:
1. A method for preparing a compound of Formula 1J,

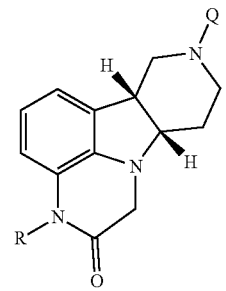

in free or salt form, wherein R is selected from H and $C_{1-4}$alkyl, and Q is selected from 4-(4-fluorophenyl)-4-oxobutyl and 3-(4-fluorophenoxy) propyl;
comprising the steps of (a) reacting a compound of Formula 1E,

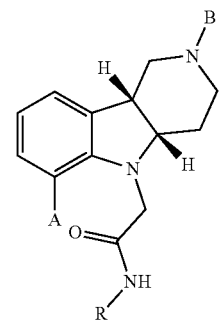

in free or salt form, wherein
(i) A is selected from Br, Cl and I;
(ii) R is selected from H and $C_{1-4}$alkyl;
(iii) B is a protecting group;

with (i) a transition metal catalyst selected from the group consisting of Groups 8-11 of the periodic table, (ii) a base, (iii) optionally an alkali metal or ammonium iodide or bromide, and (iv) a monodentate or bidentate ligand, to form an intermediate of Formula 1F,

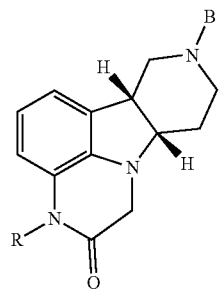

in free or salt form, wherein B and R are as defined for the compound of Formula 1E; (b) deprotecting the piperidine nitrogen of the compound of Formula 1F to yield the compound of Formula 1I,

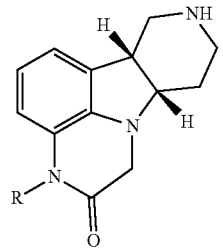

in free or salt form, wherein R is defined as for the compound of Formula 1F; and (c) alkylating the piperidine nitrogen of the compound of Formula 1I with a suitable alkylating agent to yield the compound of Formula 1J in free or salt form; and optionally (d) converting the compound of Formula 1J in free form to a compound of Formula 1J in salt form.

2. The method according to claim 1, wherein R is H.

3. The method according to claim 1, wherein Q is 3-(4-fluorophenoxy)propyl.

4. The method according to claim 1, wherein B is a group of the formula P-Z, wherein P is selected from $CH_2$, C(O), C(O)O and $S(O)_2$, and wherein Z is an optionally substituted alkyl, aryl, alkylaryl or —OR' wherein R' is alkyl, aryl, arylalkyl or heteroarylalkyl.

5. The method according to claim 1, wherein B is an acyl group.

6. The method according to claim 5, wherein the protecting group B is ethoxycarbonyl.

7. The method according to claim 1, wherein the transition metal catalyst of step (a) is a copper catalyst.

8. The method according to claim 7, wherein the transition metal catalyst of step (a) is selected from CuI, CuBr, CuCl, $Cu(OAc)_2$, $Cu_2Cl_2$, $CuBr_2$, $CuSO_4$, $Cu_2SO_4$, and $Cu_2O$.

9. The method according to claim 8, wherein the transition metal catalyst is CuI.

10. The method according to claim 1, wherein the base of step (a) is a carbonate base.

11. The method of claim 10, wherein the base of step (a) is selected from sodium carbonate, potassium carbonate, sodium bicarbonate, or potassium bicarbonate, or a mixture thereof.

12. The method according to claim 1, wherein step (a) comprises an alkali metal or ammonium iodide or bromide.

13. The method according to claim 1, wherein in step (a) the mono-dentate or bi-dentate ligand is selected from phenolic or amine ligands.

14. The method according to claim 13, wherein the ligand is selected from an optionally substituted 1,2-diamine, an optionally substituted 1,2-aminoalcohol, DBU, DBN, or DABCO.

15. The method according to claim 14, wherein the ligand is DBU.

16. The method according to claim 1, wherein the solvent for step (a) is dioxane or toluene, optionally wherein the solvent is toluene.

17. The method according to claim 16, wherein the solvent is toluene and wherein the Compound of Formula 1E is combined with the base (ii) in toluene solvent and the mixture is azeotropically distilled to remove water prior to addition of the catalyst (i) and the optional iodide (iii) and/or the ligand (iv).

18. The method according to claim 17, wherein the Compound of Formula 1F is isolated by cooling the reaction mixture to room temperature and then diluting the mixture with a non-polar solvent to precipitate the product, followed by filtration to isolate the precipitate.

19. The method according to claim 1, wherein the deprotection step (b) is an acidic hydrolysis.

20. The method according to claim 19, wherein the deprotection step (b) comprises use of hydrobromic acid in acetic acid.

21. The method according to claim 19, wherein step (b) initially yields an acid-addition salt form of the compound of Formula 1I, and wherein step (b) further comprises a neutralization step to convert the acid addition salt form of the compound of Formula 1I to the corresponding free-base form, optionally wherein the neutralization step comprises aqueous ammonia base.

22. The method according to claim 1, wherein the suitable alkylating agent of step (c) is a compound of the general formula Q-X, wherein Q is selected from 4-(4-fluorophenyl)-4-oxobutyl and 3-(4-fluorophenoxy)propyl, and wherein X is selected from chloro, bromo, iodo, $C_{1-4}$alkylsulfonyloxy and optionally substituted arylsulfonyloxy.

23. The method according to claim 22, wherein step (c) further comprises an organic base or an inorganic base.

24. The method according to claim 1, wherein the compound of Formula 1J is obtained in free base form from step (c).

25. The method according to claim 24, wherein the compound of Formula 1J in free base form is isolated from the reaction mixture by a process comprising the steps of (i) diluting the reaction mixture with an organic solvent and water, (ii) separating the organic layer and concentrating it under vacuum to a low volume, and (iii) co-evaporating the residue with a nonpolar solvent from one to five times followed by collection of the solids by filtration.

26. The method according to claim 25, wherein the crude product obtained is further purified by precipitation from a suitable solvent.

27. The method according to claim 25, wherein the crude product is slurried and filtered with acetonitrile followed by recrystallization from a binary solvent mixture.

28. The method according to claim 25, wherein the compound of formula 1J is obtained as a crystalline solid.

29. The method according to claim 1, wherein the method further comprises the step of preparing a compound of Formula 1E:

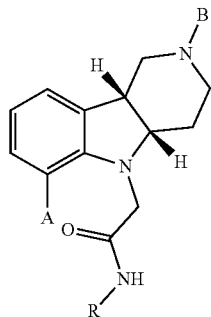

1E wherein:
(i) A is selected from Br, Cl and I;
(ii) R is selected from H and $C_{1-4}$alkyl; and
(iii) B is a protecting group;
in free or salt form,
comprising the step of N-alkylating a compound of Formula 1D:

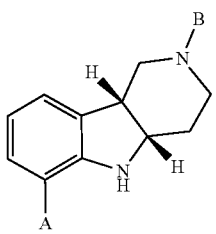

1D wherein:
(i) A is selected from Br, Cl and I; and
(ii) B is a protecting group;
in free or salt form,
with (a) a nucleophilic alkyl halide of the general formula:

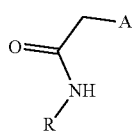

wherein:
(i) A=Cl, F, Br or I; and
(ii) R is H or $C_{1-4}$alkyl;
(b) a base, and (c) a catalyst;
wherein the base is a tertiary amine base and the catalyst is a tetraalkyl ammonium halide.

30. The method according to claim 1, wherein the transition metal catalyst of step (a) is selected from CuI, CuBr, CuCl, Cu(OAc)$_2$, Cu$_2$Cl$_2$, CuBr$_2$, CuSO$_4$, Cu$_2$SO$_4$, and Cu$_2$O, and wherein the base of step (a) is selected from alkali or alkaline earth metal carbonates or bicarbonates, or mixtures thereof; and wherein the monodentate or bidentate ligand of step (a) is selected from DBU, DBN, or DABCO, and wherein the solvent for step (a) is toluene.

31. The method according to claim 30, wherein R is H, Q is 3-(4-fluorophenoxy)propyl, and B is a group of the formula P-Z, wherein P is selected from CH$_2$, C(O), C(O)O and S(O)$_2$, and wherein Z is an optionally substituted alkyl, aryl, alkylaryl or —OR' wherein R' is alkyl, aryl, arylalkyl or heteroarylalkyl.

32. The method according to claim 31, wherein B is an acyl group selected from t-butoxycarbonyl, phenoxycarbonyl, ethoxycarbonyl, or methoxycarbonyl, or an optionally substituted benzyloxycarbonyl.

33. The method according to claim 12, wherein the alkali metal iodide or bromide is potassium iodide or tetrabutylammonium bromide.

34. The method according to claim 22, wherein X is selected from methanesulfonyloxy, benzenesulfonyloxy, and 4-nitrobenzenesulfonyloxy.

35. The method according to claim 31, wherein B is ethoxycarbonyl.

36. The method according to claim 1, wherein R is H, Q is 3-(4-fluorophenoxy)propyl, and B is a group of the formula P-Z, wherein P is C(O)O and Z is an optionally substituted alkyl, aryl, or alkylaryl.

37. The method according to claim 36, wherein the transition metal catalyst of step (a) is selected from CuI, CuBr, CuCl, Cu OAc)$_2$, Cu$_2$Cl$_2$, CuBr$_2$, CuSO$_4$, Cu$_2$SO$_4$, and Cu$_2$O, and wherein the base of step (a) is selected from alkali or alkaline earth metal carbonates or bicarbonates, or mixtures thereof; and wherein the monodentate or bidentate ligand of step (a) is selected from DBU, DBN, or DABCO.

38. The method according to claim 37, wherein the transition metal catalyst of step (a) is CuI, the base of step (a) is selected from sodium carbonate, potassium carbonate, sodium bicarbonate, or potassium bicarbonate, or a mixture thereof, the solvent for step (a) is toluene, and the ligand of step (a) is DBU.

39. The method according to claim 38, wherein B is ethoxycarbonyl.

40. The method according to claim 39, wherein the compound of Formula 1J is in tosylate salt form.

41. The method according to claim 1, wherein the compound of Formula 1J is in tosylate salt form.

* * * * *